United States Patent [19]

Fortin et al.

[11] Patent Number: 4,845,083

[45] Date of Patent: Jul. 4, 1989

[54] METHOD OF INHIBITING MAMMALIAN LEUKOTRIENE BIOSYNTHESIS

[75] Inventors: Rejean Fortin, Montreal; Cheuk K. Lau, Pierrefonds; Yvan Guindon, Closse Ile Bizard; Joshua Rokach, Laval; Christiane Yoakim, Montreal, all of Canada

[73] Assignee: Merck Frosst Canada, Inc., Kirkland, Canada

[21] Appl. No.: 1,946

[22] Filed: Jan. 9, 1987

Related U.S. Application Data

[60] Division of Ser. No. 654,991, Sep. 26, 1984, Pat. No. 4,666,907, which is a continuation-in-part of Ser. No. 539,342, Oct. 5, 1983, abandoned.

[51] Int. Cl.$^4$ .............. A61K 31/395; A61K 31/535; A61K 31/54
[52] U.S. Cl. .................... 514/80; 514/183; 514/224.8; 514/225.2; 514/225.5; 514/225.8; 514/226.2; 514/229.8
[58] Field of Search ............... 514/80, 183, 223, 224, 514/228, 229, 232, 233, 234, 236, 237, 239, 224.8, 225.2, 225.5, 225.8, 226.2, 229.8

[56] References Cited

U.S. PATENT DOCUMENTS

| | | | |
|---|---|---|---|
| 3,000,885 | 9/1961 | Cusic | 544/46 |
| 3,450,698 | 6/1969 | Farge et al. | 544/35 |
| 3,471,482 | 10/1969 | Sutton | 424/247 X |
| 3,591,692 | 7/1971 | Sutton | 424/247 |
| 3,961,055 | 6/1976 | Baget | 424/247 |
| 4,148,885 | 4/1979 | Renoux et al. | 424/162 |
| 4,667,032 | 5/1987 | Lau et al. | 544/35 |
| 4,707,473 | 11/1987 | Muchowski et al. | 514/63 |

FOREIGN PATENT DOCUMENTS

| | | |
|---|---|---|
| 2247871 | 9/1971 | Fed. Rep. of Germany . |
| 4746 | 2/1967 | France . |
| 1300486 | 12/1972 | United Kingdom . |

OTHER PUBLICATIONS

Tambi et al., J. Heterocyclic Chem., vol. 20 (1983), pp. 803–805.
Nodiff et al., J. Heterocyclic Chem., vol. 5 (1968), pp. 165–177.
Chemical Abstracts, 77p (1972), 152198y.
Collier, Can J. Med. Sci, 31 (1953), pp. 195–201.
Collier et al., Can. J. Biochem., vol. 43 (1965), pp. 105–110.
Collier et al., Can. J. Biochem & Physics, vol. 33 (1955), pp. 773–779.
Collier et al., Can. J. Res, vol. 20B (1942), pp. 284–290.
Wightman et al., Biochem. J., vol. 197 (1981), pp. 523–526.
Singh et al., Asian Med. J., vol. 19 (1976), pp. 60–66.
Fishman et al., J. Pharm. Exp. Ther., vol. 150 (1965), pp. 122–128.
Bailey et al., Ann. Rpts. Med. Chem., vol 17 (1982), pp. 203–217.
Bailey et al., Ann. Rpts. Med. Chem., vol. 16 (1981), pp. 213–227.
Baumann et al., Prostaglandins, vol. 20 (1980), pp. 627–639.
Sandler, "Inhibitors of Aarchidonic Acid Metabolism" from Enzyme Inhibitors as Drugs, Univ. Park Press, Baltimore, pp. 249–262.
Mitchell, Drug Met. Rev., vol. 13 (1982), pp. 319–343.
Ellison et al., Am. J. Vet. Res, No. 7 (1957), pp. 519–522.
Rigas et al., Prostaglandins Med. (1981), pp. 183–193.
Perel et al., Neurotoxicology (1977) Raven Press, N.Y., pp. 9–13.
Halpern, Arch. Int'l Pharm. Ther., vol. 74 (1947), pp. 314–333.
Bhargava et al., Gazz. Chem. Ital., vol. 109 (1979), pp. 201–203.
Garry et al., Biochem. Pharm., vol. 21 (1972), pp. 2801–2804.
Mitchell et al., Drug. Metab. Disp., vol. 7 (1979), pp. 399–403.
Akera et al., Biochem. Pharm., vol. 27 (1978), pp. 995–998.
Creese et al., Eur. J. Pharm., vol. 47 (1978), pp. 291–296.
Schenker et al., Progress in Drug Res., vol. 5, E. Tucker Ed., Birkhauser Verlag, Basel, Switzerland (1963), pp. 269–627.

*Primary Examiner*—Richard L. Raymond
*Attorney, Agent, or Firm*—Gabriel Lopez; Hesna J. Pfeiffer

[57] ABSTRACT

Phenothiazine derivatives and analogs thereof having the Formula I are useful as inhibitors of the biosynthesis of mammalian leukotrienes. As such, these compounds are useful therapeutic agents for treating allergic conditions, asthma, cardiovascular disorders and inflammation, and are useful as cytoprotective agents.

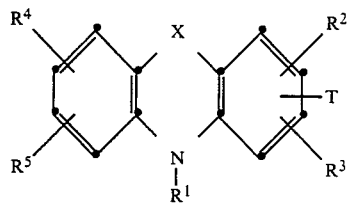

1 Claim, No Drawings

METHOD OF INHIBITING MAMMALIAN LEUKOTRIENE BIOSYNTHESIS

This is a division of application Ser. No. 654,991 filed 9-26-84, now U.S. Pat. No. 4,666,907, which in turn is a continuation-in-part of U.S. Ser. No. 539,342, filed Oct. 5, 1983, now abandoned.

Phenothiazine derivatives and analogs thereof are useful as inhibitors of the biosynthesis of mammalian leukotrienes. As such, these compounds are useful therapeutic agents for treating allergic conditions, asthma, cardiovascular disorders, inflammation and certain skin diseases.

The leukotrienes are a novel group of biologically active substances derived from arachidonic acid through the action of the 5-lipoxygenase enzyme system. There are two groups of leukotrienes derived from a common unstable precursor Leukotriene A4. The first of these are the peptido-lipid leukotrienes, the most important being Leukotrienes C4 and D4. These compounds collectively account for the biologically active material known as the slow reacting substance of anaphylaxis.

The leukotrienes are potent smooth muscle contracting agents, particularly on respiratory smooth muscle but also on other tissues (e.g., gall bladder). In addition, they promote mucous production, modulate vascular permeability changes and are potent inflammatory agents in human skin. The most important compound in the second group of leukotrienes is Leukotriene B4, a dihydroxy fatty acid. This compound is a potent chemotactic agent for neutrophils and eosinophils. It also effects other cell types such as lymphocytes and for example may modulate the action of T-suppressor cells and natural killer cells. When injected in vivo, in addition to promoting the accumulation of leukocytes, Leukotriene B4 is also a potent hyperalgesic agent and can modulate vascular permeability changes through a neutrophil dependent mechanism. See: D. M. Bailey and F. B. Casey, *Ann. Rpts. Med. Chem.* 17, 203 (1982).

As indicated above, the leukotrienes have been implicated in numerous disease states. Inhibition of leukotriene biosynthesis and/or antagonism of leukotriene action, will therefore provide a therapeutic benefit to patients suffering from leukotriene mediated disease states. These disease states include, but are not limited to; asthma; allergic conditions such as allergic rhinitis; skin diseases including psoriasis and atopic dermatitis; inflammation; gouty arthritis; gall bladder spasms; and cardiovascular disorders such as angina.

Phenothiazine derivatives of the general Formula II are known compounds:

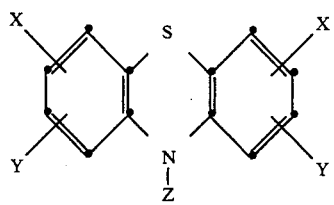

See for example; "Progress in Drug Research", Volume 5, E. Tucker, ed., Birkhauser Verlag, Basel Switzerland (1963) pages 274–383; V. A. Rigas et al., *Prostaglandins Med.* 183 (1981); J. M. Perel et al., *Neurotoxicoloqy*, Raven Press, New York, 1977, pp. 9–13; V. Fishman et al., *J. Pharm. Exp. Ther.* 150 165 (1965); *Arch. Intern. Pharm. Ther.* 74 314 (1947); N. Bhargava et al., *Gazz. Chim. Ital.* 109 201 (1979); V. F. Garry et al., *Biochem. Pharm.* 21 2801 (1972); S. C. Mitchell et al., *Drug Met. Disp.* 7 399 (1979); T. Akera et al., *Biochem. Pharm.* 27 995 (1978); I. Creese et al., *Europ. J. Pharm.*, 47 291 (1978); S. C. Mitchell, *Drug Met. Rev.*, 13 319 (1982); T. Ellison et al., *Am. J. Vet. Res.* (7) 519 (1957); K. P. Singh et al., *Asian Med. J.* 19 296 (1976) and H. B. Collier, *Can. J. Med. Sci.* 31 195 (1953).

Several derivatives of phenothiazine are known to be inhibitors of enzymes, including the 15-lipoxygenase enzyme isolated from soybeans. However, none of the compounds of Formula A are taught to have leukotriene biosynthesis inhibiting ability via the inhibition of the mammalian 5-lipoxygenase enzyme system.

It has been discovered that compounds of the Formula A type and analogs thereof are effective inhibitors of mammalian leukotriene biosynthesis and are thus useful in the treatment of conditions such as asthma, allergies, inflammation, psoriasis, and the like in mammals, especially in humans.

Compounds of the Formula A type and analogs thereof may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as CCl4 and D-galactosamine; ischemic renal failure; disease-induced hepatic damage; bile salt induced pancreatic or gastric damage; trauma- or stress-induced cell damage; and glycerol-induced renal failure.

The present invention relates to pharmaceutical compositions containing a compound of the general Formula I and a pharmaceutically acceptable carrier; a method of treatment using compounds of Formula I; and certain novel compounds of Formula I:

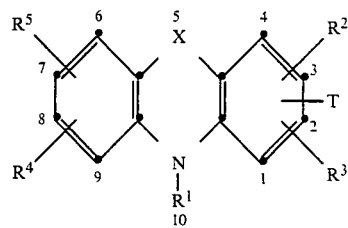

wherein: X is Se, S, SO, SO$_2$ or O; R$^1$ is H; C$_1$ to C$_6$ alkyl; C$_1$ to C$_6$ acyl; lower acyloxylower alkyl (e.g. —CH(CH$_3$)OCOC(CH$_3$)$_3$); lower alkoxy-lower alkyl (e.g. —CH(CH$_3$)OC$_2$H$_5$);

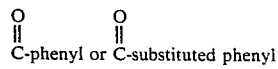
C-phenyl or C-substituted phenyl wherein substituted phenyl is as defined in the definition of R$^{16}$; carbamoyl;

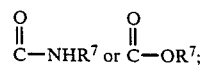
C—NHR$^7$ or C—OR$^7$;

SO$_2$-C$_6$H$_4$-p-CH$_3$; SO$_2$CH$_3$; an acyl group such that R$^1$-OH is an essential amino acid; benzyl; phenethyl; (CH$_2$)$_n$OR$^a$ wherein R$^a$ is C$_1$ to C$_6$ alkyl or phenyl and n is 1 to 5; $(CH_2)_nCOOR^6$ wherein n is 0 to 2; or lower acyloxy-lower alkoxy carbonyl (e.g. $—COOCH(O_2CCH_3)CH_3$); $R^2$, $R^3$, $R^4$ and $R^5$ are independently selected from:
(1) hydrogen;
(2) alkyl having 1 to 6 carbon atoms;
(3) alkenyl having 2 to 6 carbon atoms; and
(4) $—(CH_2)_nM$ wherein n is 0 to 6 and M is
(a) $—OR^{16}$;
(b) halogen;
(c) $—CF_3$;
(d) $—SR^{16}$;
(e) phenyl or substituted phenyl wherein substituted phenyl is as defined in the definition of $R^{16}$;
(f) $COOR^6$;
(g)

(h) tetrazole;
(i)

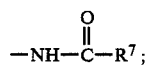

(j) $—NR^8R^9$;
(k) $—NHSO_2R^{10}$ wherein $R^{10}$ is OH, $C_1$ to $C_6$ alkyl, $C_1$ to $C_6$ alkoxy, or phenyl;
(l)

(m) $—SOR^{11}$ wherein $R^{11}$ is $C_1$ to $C_6$ alkyl; phenyl; substituted phenyl wherein substituted phenyl is as defined in the definition of $R^{16}$; $(CH_2)_mCOOR^6$ wherein m is 1 to 6; CN; formyl; or perfluoro-$C_1$ to $C_4$ alkyl;
(n) $—CONR^8R^9$;
(o) $—SO_2NR^8R^9$;
(p) $—SO_2R_{13}$ wherein $R_{13}$ is OH; $C_1$ to $C_6$ alkyl; H; phenyl; substituted phenyl wherein substituted phenyl is as defined in the definition of $R^{16}$; $(CH_2)_mCOOR^6$ wherein m is 1 to 6; CN; formyl; or perfluoro-$C_1$ to $C_4$ alkyl;
(q) $—NO_2$;
(r)

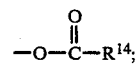

(s)

(t) $—CN$;
each $R^6$ is independently H, phenyl or $C_1$ to $C_6$ alkyl;
each $R^7$ is independently $C_1$ to $C_6$ alkyl, benzyl, phenyl, or $C_1$ to $C_6$ acyloxy-$C_1$ to $C_6$ alkyl;

each $R^8$ and each is independently H, $C_1$ to $C_4$ alkyl, phenyl, or substituted phenyl wherein substituted phenyl is as defined in the definition of $R^{16}$, or an $R^8$ and $R^9$ may be joined through the N to form a heterocycloalkyl group of 5 to 8 ring atoms;
each $R^{14}$ is independently H;
$(CH_2)_nCOOR^6$ wherein n is 0 to 4;
$C_1$ to $C_6$ alkyl; $C_1$ to $C_6$ alkoxy; $C_1$ to $C_6$ acyloxy-$C_1$ to $C_6$ alkoxy; phenyl; substituted phenyl wherein substituted phenyl is as defined in the definition of $R^{16}$; or $C_1$ to $C_6$ aminoalkyl such that $R^{14}COOH$ is an essential amino acid;
each $R^{16}$ is independently H; lower alkoxy-lower alkyl; $C_1$ to $C_6$ alkyl; benzyl; lower acyloxy-lower alkyl; phenyl; substituted phenyl wherein the substituents are selected from $C_1$ to $C_3$ alkyl, halogen, CN, $CF_3$, $COOR^6$, $CH_2COOR^6$, $(CH_2)_nNR^8R^9$ wherein n is 0 to 2, $C_1$ to $C_3$ alkoxy, and OH; $—(CH_2)_mCOOR^6$, wherein m is 0 to 6; CN; formyl; perfluoroalkyl; or $CH_2—R^{12}$ wherein $R^{12}$ is $C_1$ to $C_5$ alkyldimethylamino or phenyl; and T is hydrogen or $—OR^{15}$, where $R^{15}$ is hydrogen, $C_1$ to $C_6$ alkyl, $C_1$ to $C_6$ alkylayl, phenylacyl, substituted phenyl-acyl wherein substituted phenyl is as defined in the definition of $R^{16}$, or arylsulfonyl.

The numbers surrounding Formula I designate the substituent positions, and $R^2$, $R^3$, $R^4$, $R^5$ and T may be positioned anywhere in the structure except at position 10.

The term alkyl, unless otherwise indicated, includes straight chain, branched chain and cycloalkyl groups of the number of carbon atoms shown. The term halogen, unless otherwise indicated, includes Cl, Br, I and F.

The term lower as applied to the terms alkyl, acyl, alkoxy, acyloxy, and the like, means a group having 1 to 6 carbon atoms and preferably 1 to 4 carbon atoms. The term phenylacyl means a group having the formula

The term aryl includes cyclic structures having the requisite degree of unsaturation to show a characteristic "aromatic" downfield proton NMR spectrum. Examples include phenyl, substituted phenyl (as defined above in the definition of $R^{16}$) naphthyl, anthracenyl, and the like, and include heteroaryl species containing one or more of the heteroatoms selected from O, N or S.

The term essential amino acid is employed to include the following amino acids; lysine, tryptophan, histidine, phenylalanine, leucine, isoleucine, threonine, methionine, valine, arginine, alanine, proline, glycine, serine, cysteine, tyrosine, asparagine, glutamine, aspartic acid and glutamic acid.

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

A preferred composition is comprised of compounds of the Formula I wherein:
X is S, SO, $SO_2$ or O;

$R^1$ is H; $C_1$ to $C_6$ alkyl; $C_1$ to $C_6$ acyl; lower acyloxy-lower alkyl; lower alkoxy-lower alkyl;

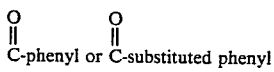
C-phenyl or C-substituted phenyl wherein substituted phenyl is as defined in the definition of $R^{16}$; carbamoyl;

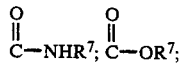
C—NHR$^7$; C—OR$^7$;

$SO_2$—$C_6H_4$—p—$CH_3$; $SO_2CH_3$; an acyl group such that $R^1$—OH is an essential amino acid; benzyl; phenethyl; $(CH_2)_nOR^a$ wherein $R^a$ is $C_1$ to $C_6$ alkyl or phenyl and n is 1 to 5; $(CH_2)_nCOOR^6$ wherein n is 0 to 2; or lower acyloxy-lower alkoxy carbonyl;

$R^2$, $R^3$, $R^4$ and $R^5$ are independently selected from:
(1) hydrogen;
(2) alkyl having 1 to 6 carbon atoms;
(3) alkenyl having 2 to 6 carbon atoms; and
(4) —$(CH_2)_nM$ wherein n is 0 to 2 and M is
(a) —$OR^{16}$;
(b) halogen;
(c) —$CF_3$;
(d) —$SR^{16}$;
(e) phenyl or substituted phenyl wherein substituted phenyl is as defined in the definition of $R^{16}$;
(f) $COOR^6$;
(g)

C—$R^{14}$;

(h) tetrazole;
(i)

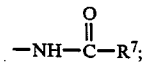
—NH—C—$R^7$;

(j) —$NR^8R^9$;
(k) —$NHSO_2R^{10}$ wherein $R^{10}$ is OH, $C_1$ to $C_6$ alkyl, $C_1$ to $C_6$ alkoxy, or phenyl;
(l)

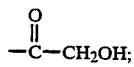
—C—$CH_2OH$;

(m) —$SOR^{11}$ wherein $R^{11}$ is $C_1$ to $C_6$ alkyl; phenyl; substituted phenyl wherein substituted phenyl is as defined in the definition of $R^{16}$; $(CH_2)_mCOOR^6$ wherein m is 1 to 6; CN; formyl or perfluoro-$C_1$ to $C_4$ alkyl;
(n) —$CONR^8R^9$;
(o) —$SO_2NR^8R^9$;
(p) —$SO_2R^{13}$ wherein $R^{13}$ is OH; $C_1$ to $C_6$ alkyl; H; phenyl; substituted phenyl wherein substituted phenyl is as defined in the definition of $R^{16}$; $(CH_2)_mCOOR^6$ wherein m is 1 to 6; CN; formyl or perfluoro-$C_1$ to $C_4$ alkyl;
(q) —$NO_2$;
(r)

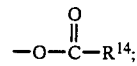
—O—C—$R^{14}$;

(s)

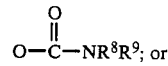
O—C—$NR^8R^9$; or (t) —CN;

each $R^6$ is independently H, phenyl or $C_1$ to $C_6$ alkyl;
each $R^7$ is independently $C_1$ to $C_6$ alkyl, benzyl, phenyl, or $C_1$ to $C_6$ acyloxy-$C_1$ to $C_6$ alkyl;
each $R^8$ and each $R^9$ is independently alkyl, phenyl, or substituted phenyl wherein substituted phenyl is as defined in the definition of $R^{16}$, or an $R^8$ and an $R^9$ may be joined through the N to which they are attached form a heterocycloalkyl group of 5 to 8 ring atoms;
each $R^{14}$ is independently $(CH_2)_nCOOR^6$ wherein n is 0 to 4; $C_1$ to $C_6$ alkyl; $C_1$ to $C_6$ alkoxy; $C_1$ to $C_6$ acyloxy-$C_1$ to $C_6$ alkoxy, phenyl; substituted phenyl wherein substituted phenyl is as defined in the definition of $R^{16}$; or $C_1$ to $C_6$ aminoalkyl such that $R^{14}COOH$ is an essential amino acid;
each $R^{16}$ is independently H; lower alkoxy-lower alkyl; $C_1$ to $C_6$ alkyl; benzyl; lower acyloxy-lower alkyl; phenyl; substituted phenyl wherein the substituents are selected from $C_1$ to $C_3$ alkyl, halogen, CN, $CF_3$, $COOR^6$, $CH_2COOR^6$, $(CH_2)_nNR^8R^9$ wherein n is 0 to 2, $C_1$ to $C_3$ alkoxy, and OH; —$(CH_2)_mCOOR^6$, wherein m is 0 to 6; CN; formyl; perfluoroalkyl; or $CH_2$—$R^{12}$ wherein $R^{12}$ is $C_1$ to $C_5$ alkyldimethylamino or phenyl;

and T is hydrogen or —$OR^{15}$, where $R^{15}$ is hydrogen, $C_1$ to $C_6$ alkyl, $C_1$ to $C_6$ alkylacyl, phenylacyl, substituted phenylacyl wherein substituted phenyl is as defined in the definition of $R^{16}$, or arylsulfonyl.

More preferred compounds for use in the compositions of the present invention are those of the Formula I wherein:

X is S, SO, $SO_2$ or O;

$R^1$ is H; $C_1$ to $C_6$ alkyl; $C_1$ to $C_6$ acyl; lower acyloxy-lower alkyl; lower alkoxy-lower alkyl;

C-phenyl; C-substituted phenyl wherein substituted phenyl is as defined in the definition of $R^{16}$; carbamoyl;

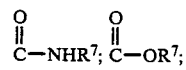
C—NHR$^7$; C—OR$^7$;

$SO_2$—$C_6H_4$—p—$CH_3$; $SO_2CH_3$; an acyl group such that $R^1$—OH is an essential amino acid; benzyl; phenethyl; $(CH_2)_nOR^a$ wherein $R^a$ is $C_1$ to $C_6$ alkyl or phenyl and n is 1 to 5; $(CH_2)_nCOOR^6$ wherein n is 0 to 2; or lower acyloxy-lower alkoxy carbonyl;

$R^2$, $R^3$, $R^4$ and $R^5$ are independently selected from:
(1) hydrogen;
(2) alkyl having 1 to 6 carbon atoms; and
(3) —$(CH_2)_nM$ wherein n is 0 to 1 and M is
(a) —$OR^{16}$;

(b) halogen;
(c) —CF$_3$;
(d) —SR$^{16}$;
(e) phenyl or substituted phenyl wherein substituted phenyl is as defined in the definition of
(f) COOR$^6$;
(g)

$$\overset{O}{\underset{\|}{C}}-R^{14};$$

(h) tetrazole;
(i)

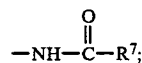
$$-NH-\overset{O}{\underset{\|}{C}}-R^7;$$

(j) —NR$^8$R$^9$;
(k) —NHSO$_2$R$^{10}$ wherein R$^{10}$ is OH, C$_1$ to C$_6$ alkyl; C$_1$ to C$_6$ alkoxy, or phenyl;
(l)

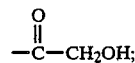
$$-\overset{O}{\underset{\|}{C}}-CH_2OH;$$

(m) —SOR$^{11}$ wherein R$^{11}$ is C$_1$ to C$_6$ alkyl; phenyl; substituted phenyl wherein substituted phenyl is as defined in the definition of R$^{16}$; (CH$_2$)$_m$COOR$^6$ wherein m is 1 to 6; CN; formyl; or perfluoro-C$_1$ to C$_4$ alkyl;
(n) —CONR$^8$R$^9$;
(o) —SO$_2$NR$^8$R$^9$;
(p) —SO$_2$R$_{13}$ wherein R$_{13}$ is OH; C$_1$ to C$_6$ alkyl; H; phenyl; substituted phenyl wherein substituted phenyl is as defined in the definition of R$^{16}$; (CH$_2$)$_m$COOR$^6$ wherein m is 1 to 6; CN; formyl; or perfluoro-C$_1$ to C$_4$ alkyl;
(q) —NO$_2$;
(r)

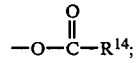
$$-O-\overset{O}{\underset{\|}{C}}-R^{14};$$

(s)

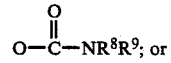
$$-O-\overset{O}{\underset{\|}{C}}-NR^8R^9;\text{ or}$$

(t) —CN;
each R$^6$ is independently H, phenyl or C$_1$ to C$_6$ alkyl;
each R$^7$ is independently C$_1$ to C$_6$ alkyl, benzyl, phenyl or C$_1$ to C$_6$ acyloxy-C$_1$ to C$_6$ alkyl;
each R$^8$ and each R$^9$ is independently H, C$_1$ to C$_4$ alkyl, phenyl, substituted phenyl wherein substituted phenyl is as defined in the definition of R$^{16}$, or an R$^8$ and an R$^9$ may be joined through the N to which they are attached to form a heterocycloalkyl group of 5 to 8 ring atoms;
each R$^{14}$ is independently H; (CH$_2$)$_n$COOR$^6$ wherein n is 0 to 4; C$_1$ to C$_6$ alkyl; C$_1$ to C$_6$ alkoxy; C$_1$ to C$_6$ acyloxy-C$_1$ to C$_6$ alkoxy; phenyl; substituted phenyl wherein substituted phenyl is as defined in the definition of R$^{16}$; or C$_1$ to C$_6$ aminoalkyl such that R$^{14}$COOH is an essential amino acid;

each R$^{16}$ is independently H; lower alkoxy-lower alkyl; C$_1$ to C$_6$ alkyl; benzyl; lower acyloxy-lower alkyl; phenyl; substituted phenyl wherein the substituents are selected from C$_1$ to C$_3$ alkyl, halogen, CN, CF$_3$, COOR$^6$, CH$_2$COOR$^6$, (CH$_2$)$_n$NR$^8$R$^9$ wherein n is 0 to 2, C$_1$ to C$_3$ alkoxy, and OH; —(CH$_2$)$_m$COOR$^6$, wherein m is 0 to 6; CN; formyl; perfluoroalkyl; or CH$_2$—R$^{12}$ wherein R$^{12}$ is C$_1$ to C$_5$ alkyldimethylamino or phenyl;
and T is hydrogen or —OR$^{15}$, wherein R$^{15}$ is hydrogen, C$_1$ to C$_6$ alkyl, C$_1$ to C$_6$ alkylacyl, phenylacyl, substituted phenyl-acyl wherein substituted phenyl is as defined in the definition of R$^{16}$, or arylsulfonyl.

Most preferred compounds for use in the compositions of the present invention are compounds of the Formula I wherein:
X is S or O;
R$^1$ is H; C$_1$ to C$_6$ alkyl; C$_1$ to C$_6$ acyl; lower acyloxy-lower alkyl; lower alkoxy-lower alkyl

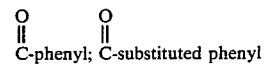
$$\overset{O}{\underset{\|}{C}}\text{-phenyl; }\overset{O}{\underset{\|}{C}}\text{-substituted phenyl}$$

wherein substituted phenyl is as defined in the definition of R$^{14}$; carbamoyl;

$$\overset{O}{\underset{\|}{C}}-NHR^7;\overset{O}{\underset{\|}{C}}-OR^7;$$

(CH$_2$)$_n$OR$^a$ is C$_1$ to C$_6$ alkyl or phenyl and n is 1 to 5; (CH$_2$)$_n$COOR$^6$ wherein n is 0 to 2; or lower acyloxy-lower alkoxy carbonyl;
R$^2$, R$^3$, R$^4$ and R$^5$ are independently selected from:
(1) hydrogen;
(2) alkyl having 1 to 6 carbon atoms; and
(3) —(CH$_2$)$_n$M
wherein n is 0 and M is
(a) —OR$^{16}$;
(b) halogen;
(c) —CF$_3$;
(d) —SR$^{16}$;
(e) COOR$^6$;
(f)

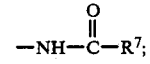
$$-NH-\overset{O}{\underset{\|}{C}}-R^7;$$

(g) —NR$^8$R$^9$;
(h) —SOR$^{11}$ wherein R$^{11}$ is C$_1$ to C$_6$ alkyl or perfluoro-C$_1$ to C$_4$ alkyl;
(i) —SO$_2$R$^{13}$ wherein R$^{13}$ is C$_1$ to C$_6$ alkyl or perfluoro-C$_1$ to C$_4$ alkyl;
(j)

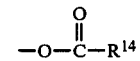
$$-O-\overset{O}{\underset{\|}{C}}-R^{14}$$

wherein R$^{14}$ is H, C$_1$ to C$_6$ alkyl, phenyl or phenyl substituted by C$_1$ to C$_3$ alkyl, halogen, CN, CF$_3$; COOR$^6$ CH$_2$COOR$^6$ (CH$_2$)$_u$NR$^8$R$^9$ wherein u is 0 to 2, C$_1$ to C$_3$ alkoxy or OH;
(k)

(l) —CN;

each $R^6$ is independently H, phenyl or $C_1$ to $C_6$ alkyl;

each $R^7$ is independently $C_1$ to $C_6$ alkyl, benzyl, phenyl, or $C_1$ to $C_6$ acyloxy-$C_1$ to $C_6$ alkyl;

each $R^8$ and each $R^9$ is independently H; $C_1$ to $C_4$ alkyl; phenyl; or substituted phenyl wherein substituted phenyl is as defined in the definition of $R^{14}$; or $R^8$ and $R^9$ may be joined through the N to which they are attached to form a heterocycloalkyl group of 5 to 8 ring atoms;

each $R^{16}$ is independently H; $C_1$ to $C_6$ alkyl; benzyl; lower acyloxy-lower alkyl; or perfluoro-$C_1$ to $C_4$ alkyl;

and T is hydrogen or —$OR^{15}$, where $R^{15}$ is hydrogen, $C_1$ to $C_6$ alkyl, $C_1$ to $C_6$ alkylacyl, phenylacyl, or substituted phenyl-acyl wherein substituted phenyl is as defined in the definition of $R^{14}$.

Another preferred group of compounds for use in the compositions of the present invention are compounds of the Formula I wherein:

X is O or S, $R^1$ is hydrogen, $C_1$ to $C_4$ alkyl, $C_1$ to $C_4$ alkylacyl, —$(CH_2)_n OR^a$ wherein $R^a$ is $C_1$ to $C_4$ alkyl or phenyl and n is 1 to 3, lower acyloxy-lower alkyl, lower alkoxy carbonyl, or lower acyloxy-lower alkoxy carbonyl;

$R^2$, $R^3$, $R^4$ and $R^5$ are each independently selected from hydrogen; halogen; hydroxyl; $C_1$ to $C_3$ alkyl; $C_1$ to $C_3$ alkoxy; $C_1$ to $C_3$ lower alkylthio; $C_1$ to $C_5$ acyloxy; benzoyloxy; trihalo $C_1$ to $C_3$ alkyl; aminoloweralkyl; $C_1$ to $C_5$ acyl; $(CH_2)_m COOR^6$, wherein m is 0 to 4 and $R^6$ is H, phenyl or $C_1$ to $C_6$ alkyl; and lower acyloxy-lower alkoxycarbonyloxy; and T is as defined above.

Another particularly preferred group of compounds for use in the compositions of the present invention are compounds of Formula III:

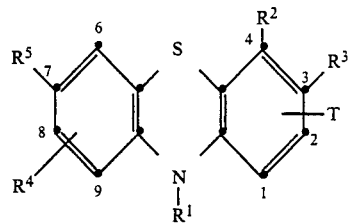

wherein:

$R^1$ is H, $C_1$ to $C_4$ acyl, lower acyloxy-lower alkyl, or lower acyloxy-lower alkoxycarbonyl;

$R^2$ is halogen (F, Cl, Br or I);

$R^3$ is OH, $C_1$ to $C_5$ acyloxy, benzoyloxy, or lower acyloxy-lower alkoxycarbonyloxy;

$R^4$ is H, OH, lower alkoxy or lower acyloxy and is located at either position 1 or position 2;

$R^5$ is OH, lower alkoxy or lower acyloxy;

T is hydrogen or lower alkoxy.

Examples of the Formula I compounds useful in the present compositions are tabulated below. In Table I, the number preceding the $R^2$–$R^5$ and T definitions signifies that groups position on the ring system. Standard abbreviations are used, for example, Ph for phenyl, Bz for benzoyl, Ts for p-toluenesulfonyl, Me for methyl, Bu for butyl, Et for ethyl and Ac for acetyl.

TABLE I

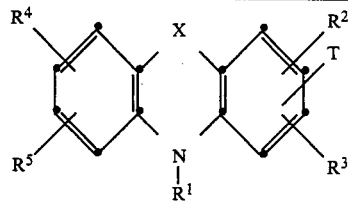

| Compound[a] | X | $R^1$ | $R^2$ | $R^3$ | $R^4$ | $R^5$ | T |
|---|---|---|---|---|---|---|---|
| 1 | S | H | H | H | H | H | H |
| 2 | S | Me | 2-t-Bu | 4-t-Bu | H | H | 1-OH |
| 3 | S | Me | 2-t-Bu | 4-t-Bu | H | H | 1-OMe |
| 4 | S | Me | 2-t-Bu | 4-t-Bu | H | H | 1-OAc |
| 5 | S | Ac | 2-t-Bu | 4-t-Bu | H | H | 1-OH |
| 6 | S | H | 2-t-Bu | 4-t-Bu | H | H | 1-OMe |
| 7 | S | H | 2-t-Bu | 4-t-Bu | H | H | 1-OAc |
| 8 | O | H | 2-t-Bu | 4-t-Bu | H | H | 1-OH |
| 9 | S | $CH_2OAc$ | 2-t-Bu | 4-t-Bu | H | H | 1-OH |
| 10 | S | H | 1-Cl | H | H | H | 3-OH |
| 11 | S | H | 1-Cl | H | H | H | 3-OAc |
| 12 | S | H | 1-Cl | H | H | H | 3-OMe |
| 13[1] | S | Me | 1-Cl | H | H | H | 3-OH |
| 14[1] | S | Me | 1-Cl | H | H | H | 3-OAc |
| 15 | S | Me | 1-Cl | H | H | H | 3-OMe |
| 16 | S | $CH_2OAc$ | 1-Cl | H | H | H | 3-OMe |
| 17 | S | $CH_2OAc$ | 1-Cl | H | H | H | 3-OAc |
| 18 | O | H | 1-Cl | H | H | H | 3-OH |
| 19 | O | Me | 1-Cl | H | H | H | 3-OH |
| 20 | O | Me | 1-Cl | H | H | H | 3-OAc |
| 21 | O | Me | 1-Cl | H | H | H | 3-OMe |
| 22 | O | Ac | 1-Cl | H | H | H | 3-OAc |
| 23 | O | $CH_2OAc$ | 1-Cl | H | H | H | 3-OMe |
| 24 | Se | Me | 1-Cl | H | H | H | 3-OMe |
| 25 | SO | H | 1-Cl | H | H | H | 3-OH |
| 26 | SO | H | 1-Cl | H | H | H | 3-OMe |
| 27 | SO | H | 1-Cl | H | H | H | 3-OAc |

TABLE I-continued

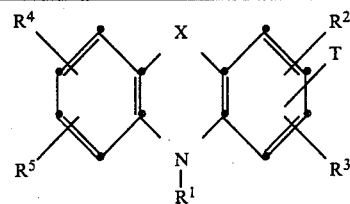

| Compound[a] | X | R[1] | R[2] | R[3] | R[4] | R[5] | T |
|---|---|---|---|---|---|---|---|
| 28 | SO | Me | 1-Cl | H | H | H | 3-OH |
| 29 | SO | Me | 1-Cl | H | H | H | 3-OAc |
| 30 | SO | Me | 1-Cl | H | H | H | 3-OMe |
| 31[1] | SO$_2$ | H | 1-Cl | H | H | H | 3-OH |
| 32 | SO$_2$ | H | 1-Cl | H | H | H | 3-OAc |
| 33 | SO$_2$ | H | 1-Cl | H | H | H | 3-OMe |
| 34 | SO$_2$ | Me | 1-Cl | H | H | H | 3-OAc |
| 35 | SO$_2$ | Me | 1-Cl | 7-OCH$_2$CO$_2$H | H | H | 3-OAc |
| 36 | SO$_2$ | Me | 1-Cl | H | H | H | 3-OMe |
| 37[1] | SO$_2$ | Ac | 1-Cl | H | H | H | 3-OH |
| 38[1] | SO$_2$ | Ac | 1-Cl | H | H | H | 3-OAc |
| 39 | SO$_2$ | Ac | 1-Cl | H | H | H | 3-OMe |
| 40 | SO | Ac | 1-Cl | H | H | H | 3-OH |
| 41 | SO | Ac | 1-Cl | H | H | H | 3-OAc |
| 42 | SO | Ac | 1-Cl | H | H | H | 3-OMe |
| 43 | SO$_2$ | CH$_2$OAc | 1-Cl | H | H | H | 3-OH |
| 44 | SO$_2$ | CH$_2$OAc | 1-Cl | H | H | H | 3-OAc |
| 45 | SO$_2$ | CH$_2$OAc | 1-Cl | H | H | H | 3-OMe |
| 46 | S | CH$_2$Ph | H | H | H | H | H |
| 47 | S | Me | H | H | H | H | H |
| 48 | S | Ac | H | H | H | H | H |
| 49 | S | CH$_2$OAc | H | H | H | H | H |
| 50 | O | H | H | H | H | H | H |
| 51 | O | Me | H | H | H | H | H |
| 52 | O | Ac | H | H | H | H | H |
| 53 | Se | H | H | H | H | H | H |
| 54 | Se | Me | H | H | H | H | H |
| 55 | Se | Ac | H | H | H | H | H |
| 56 | Se | CH$_2$OAc | H | H | H | H | H |
| 57 | SO | H | H | H | H | H | H |
| 58 | SO | Me | H | H | H | H | H |
| 59 | SO$_2$ | Ac | H | H | H | H | H |
| 60 | S | H | H | H | H | H | 3-OH |
| 61 | S | H | H | H | H | H | 3-OAc |
| 62 | S | H | H | H | H | H | 3-OMe |
| 63 | S | Me | H | H | H | H | 3-OAc |
| 64 | S | Me | H | H | H | H | 3-OH |
| 65 | S | Me | H | H | H | H | 3-OMe |
| 66 | S | Ac | H | H | H | H | 2-OH |
| 67 | S | Ac | H | H | H | H | 3-OAc |
| 68 | S | Ac | H | H | H | H | 3-OMe |
| 69 | S | CH$_2$OAc | H | H | H | H | 3-OH |
| 70 | S | CH$_2$OAc | H | H | H | H | 3-OAc |
| 71 | S | CH$_2$OAc | H | H | H | H | 3-OMe |
| 72 | Same as compounds 60–71 but X = O | | | | | | |
| 73[1] | Same as compounds 60–71 but X = Se | | | | | | |
| 74 | S | H | 4-Cl | H | H | H | 3-OH |
| 75 | S | H | 4-Cl | H | H | H | 3-OMe |
| 76[1] | S | H | 4-Cl | H | H | H | 3-OAc |
| 77 | S | Me | 4-Cl | H | H | H | 3-OH |
| 78[1] | S | Me | 4-Cl | H | H | H | 3-OAc |
| 79[1,2] | S | Me | 4-Cl | H | H | H | 3-OMe |
| 80[1,2] | S | Ac | 4-Cl | H | H | H | 3-OH |
| 81[1,2] | S | Ac | 4-Cl | H | H | H | 3-OAc |
| 82[1] | S | Ac | 4-Cl | H | H | H | 3-OMe |
| 83 | S | Me | 4-Cl | H | H | H | 3-O—Bz |
| 84[1] | S | Me | 4-Cl | H | H | H | 3-OCOCH(Me)$_2$ |
| 85 | S | Me | 4-Cl | H | H | H | 3-OCOC(Me)$_3$ |
| 86[1,2] | SO$_2$ | H | 4-Cl | H | H | H | 3-OH |
| 87[1] | SO$_2$ | H | 4-OH | H | H | H | 3-OH |
| 88[1,2] | SO$_2$ | H | 4-Cl | H | H | H | 3-OAc |
| 89 | SO$_2$ | H | 4-Cl | H | H | H | 3-OMe |
| 90 | SO$_2$ | Me | 4-Cl | H | H | H | 3-OH |
| 91 | SO$_2$ | Me | 4-Cl | H | H | H | 3-OAc |
| 92[1] | SO$_2$ | Me | 4-Cl | H | H | H | 3-OMe |
| 93[1,2] | SO$_2$ | Ac | 4-Cl | H | H | H | 3-OH |
| 94[1,2] | SO$_2$ | Ac | 4-Cl | H | H | H | 3-OAc |
| 95 | SO$_2$ | Ac | 4-Cl | H | H | H | 3-OMe |
| 96 | S | CH$_2$OAc | 4-Cl | H | H | H | H |
| 97 | S | CH$_2$OAc | 4-Cl | H | H | H | 3-OH |

TABLE I-continued

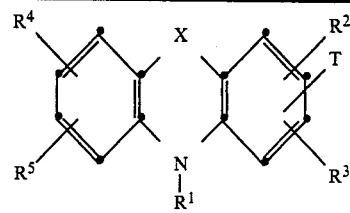

| Compound[a] | X | R[1] | R[2] | R[3] | R[4] | R[5] | T |
|---|---|---|---|---|---|---|---|
| 98 | S | CH$_2$OAc | 4-Cl | H | H | H | 3-OAc |
| 99 | S | CH$_2$OAc | 4-Cl | H | H | H | 3-OMe |
| 100 | SO$_2$ | CH$_2$OAc | 4-Cl | H | H | H | 3-OH |
| 101 | SO$_2$ | CH$_2$OAc | 4-Cl | H | H | H | 3-OAc |
| 102 | SO$_2$ | CH$_2$OAc | 4-Cl | H | H | H | 3-OMe |
| 103 | Same as compounds 74–103 but X = SO | | | | | | |
| 104 | Same as compounds 74–103 but X = O | | | | | | |
| 105 | Same as compounds 74–103 but R$_4$ is 7-Cl | | | | | | |
| 106 | Same as compound 105 but X = O | | | | | | |
| 107 | Same as compounds 74–103 but R$_4$ is 7-OMe | | | | | | |
| 108 | Same as compound 107 but X = O | | | | | | |
| 109 | Same as compounds 74–103 but R$_4$ is 7-(C$_1$-C$_6$ alkyl) | | | | | | |
| 110 | Same as compound 109 but X = O | | | | | | |
| 111 | Same as compounds 74–103 but R$_4$ is 7-(COMe) | | | | | | |
| 112 | Same as compound 111 but X = O | | | | | | |
| 113 | Same as compounds 74–103 but R$_4$ is 7-[(CH$_2$)$_m$COOR], wherein m is 0-4 | | | | | | |
| 114 | Same as compound 113 but X = O | | | | | | |
| 115 | Same as compounds 74–103 but R$_4$ is 9-Cl | | | | | | |
| 116 | S | H | 4-Et | H | H | H | 3-OH |
| 117 | S | Me | 4-Et | H | H | H | 3-OCOCH$_2$Ph |
| 118 | S | Me | 4-Et | H | H | H | 3-OAc |
| 119 | S | Me | 4-Et | H | H | H | 3-OMe |
| 120 | S | H | 4-OEt | H | H | H | 3-OH |
| 121 | S | H | 4-OEt | H | H | H | 3-OMe |
| 122 | S | Me | 4-OEt | H | H | H | 3-OMe |
| 123 | S | Me | 4-OEt | H | H | H | 3-OAc |
| 124[1] | S | H | 2-OEt | 7-OEt | H | H | 3-OH |
| 125 | S | H | 2-OEt | 7-OEt | H | H | 3-OMe |
| 126 | S | Me | 2-OEt | 7-OEt | H | H | 3-OMe |
| 127 | S | Me | 2-OEt | 7-OEt | H | H | 3-OAc |
| 128 | S | H | H | H | H | H | 3-OAc |
| 129 | S | Me | H | H | H | H | 3-OAc |
| 130 | S | Ac | H | H | H | 3-Ac | 3-OAc |
| 131 | S | H | 7-Ac | H | H | 3-Ac | H |
| 132 | S | Me | 7-Ac | H | H | 3-Ac | H |
| 133 | S | Ac | 7-Ac | H | H | 3-Ac | H |
| 134 | S | CH$_2$OAc | 7-Ac | H | H | 3-Ac | H |
| 135 | S | H | 2-Me | 4-Cl | H | H | 3-OH |
| 136 | S | Me | 2-Me | 4-Cl | H | H | 3-OAc |
| 137 | S | H | 7-Me | 2-Me | H | H | 3-OH |
| 138 | S | Me | 7-Me | 2-Me | H | H | 3-OAc |
| 139[1] | S | H | 2-OEt | 4-Cl | H | H | 3-OH |
| 140 | S | Me | 2-OEt | 4-Cl | H | H | 3-OAc |
| 141 | S | H | 2-S—n-Bu | 4-Cl | H | H | 3-OH |
| 142 | S | Me | 2-S—n-Bu | 4-Cl | H | H | 3-OAc |
| 143 | S | Me | 4-S—n-Bu | H | H | H | 3-OAc |
| 144 | S | Me | 2-O—Me | 4-Br | H | H | 3-OAc |
| 145 | S | Me | 2-O—Me | 4-Cl | H | H | 3-OAc |
| 146 | S | Me | 2-O—Me | 4-Br | H | H | 3-OH |
| 147[1] | S | H | 2-O—Me | 3-OH | H | H | 7-OMe |
| 148 | S | H | 1-OMe | 3-OH | H | H | 7-OMe |
| 149 | S | H | 2-OMe | 3-OH | 1-Br | H | 7-OMe |
| 150 | S | H | 1-OMe | 3-OH | 2-Br | H | 7-OMe |
| 151[1] | S | H | 1-OMe | 3-OH | 4-Br | H | 7-OMe |
| 152 | S | H | 1-OMe | 3-OH | 2-Cl | H | 7-OMe |
| 153[1] | S | H | 1-OMe | 3-OH | 4-Cl | H | 7-OMe |
| 154 | S | H | 2-OMe | 3-OH | 1-Cl | H | 7-OMe |
| 155[1] | S | H | 2-OMe | 3-OH | 4-Cl | H | 7-OMe |
| 156 | S | H | 2-OEt | 3-OH | 1-Br | H | 7-OEt |
| 157[1] | S | H | 2-OEt | 3-OH | 4-Br | H | 7-OEt |
| 158 | S | H | 2-OEt | 3-OH | 1-Cl | H | 7-OEt |
| 159[1] | S | H | 2-OEt | 3-OH | 4-Cl | H | 7-OEt |
| 160 | S | H | 2-OMe | 3-OH | 1-Br | 7-OMe | 9-OMe |
| 161 | S | H | 2-OMe | 3-OH | 4-Br | 7-OMe | 8-OMe |
| 162[1] | S | H | 2-OMe | 3-OH | 4-F | H | 7-OMe |
| 163[1] | S | H | 2-OMe | 3-OH | 4-CF$_3$ | H | 7-OMe |
| 164[1] | S | H | 2-OMe | 3-OH | 4-Br | H | 7-OEt |
| 165[1] | S | H | 2-OMe | 3-OH | 4-Cl | H | 7-OEt |
| 166 | S | H | 2-OMe | 3-OH | 4-F | H | 7-OEt |
| 167 | S | H | 2-OMe | 3-OH | 4-I | H | 7-OMe |

TABLE I-continued

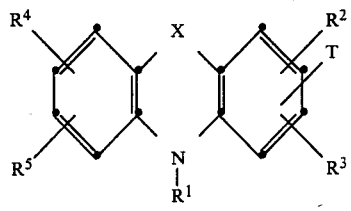

| Compound[a] | X | R[1] | R[2] | R[3] | R[4] | R[5] | T |
|---|---|---|---|---|---|---|---|
| 168 | S | H | 2-OMe | 3-OH | 4-CF$_3$ | H | 7-OEt |
| 169[1] | S | H | 2-OEt | 3-OH | 4-Br | H | 7-OMe |
| 170[1] | S | H | 2-OEt | 3-OH | 4-Cl | H | 7-OMe |
| 171 | S | H | 2-OEt | 3-OH | 4-F | H | 7-OMe |
| 172 | S | H | 2-OEt | 3-OH | 4-CF$_3$ | H | 7-OMe |
| 173 | S | H | 1-OMe | 2-OMe | 3-OH | 4-Br | 7-OMe |
| 174 | S | H | 1-OMe | 3-OH | H | H | 2-OMe |
| 175 | S | H | 1-OMe | 3-OH | 4-Br | H | 2-OMe |
| 176 | Same as compounds 147–175 but X = O | | | | | | |
| 177 | Same as compounds 147–175 but X = SO$_2$ | | | | | | |
| 178[1] | S | H | 2-SMe | 3-OH | 4-Br | H | 7-OMe |
| 179[1] | S | H | 2-OMe | 3-OH | 4-Br | 7-SMe | H |
| 180 | SO$_2$ | H | 2-SO$_2$Me | 3-OH | 4-Br | H | 7-OMe |
| 181 | Same as compounds 147–175 but X = SO | | | | | | |
| 182[1] | S | H | 4-Cl | H | H | H | 3-OBz |
| 183[1] | S | H | 4-Cl | H | H | H | 3-OCOCH(Me)$_2$ |
| 184[1] | S | Ac | H | H | 7-F | H | 3-OAc |
| 185[1] | S | Me | H | H | 7-Me | H | 3-OMe |
| 186[1] | S | H | H | H | 7-F | H | 3-OAc |
| 187[1] | S | Me | H | H | 9-Cl | H | 3-OMe |
| 188[1] | S | Me | H | H | 9-Cl | H | 3-OAc |
| 189[1] | S | Me | H | H | 7-Me | H | 3-OAc |
| 190[1] | S | H | H | H | 9-Cl | H | 3-OAc |
| 191[1] | S | H | H | 4-CF$_3$ | H | H | 3-OAc |
| 192[1] | S | H | H | 4-Cl | H | H | 3-OTs |
| 193[1] | S | Ac | H | 4-Cl | 7-F | H | 3-OMe |
| 194[1] | S | Ac | H | 4-Cl | 7-F | H | 3-OH |
| 195[1] | S | Me | H | 4-Cl | 7-F | H | 3-OMe |
| 196[1] | SO | H | H | H | H | H | 3-OAc |
| 197[1,2] | SO$_2$ | H | H | H | H | H | 3-OAc |
| 198[1,2] | SO$_2$ | H | H | H | H | H | 3-OH |
| 199[1] | SO$_2$ | H | H | H | 7-F | H | 3-OAc |
| 200[1] | SO$_2$ | H | H | 4-Cl | H | H | 3-OTs |
| 201[1] | S | H | 1-OMe | 2-OMe | 4-Me | H | 3-OH |
| 202[1] | S | H | 1-OMe | 2-OMe | 4-Me | H | 3-OAc |
| 203[1] | SO$_2$ | H | 1-OMe | 2-OMe | 4-Me | H | 3-OH |
| 204[1] | SO$_2$ | H | 4-OMe | H | H | H | 3-OH |
| 205[1] | S | H | 2-OMe | 3-OH | 4-Br | 7-OMe | H |
| 206[1] | S | H | 2-OMe | 3-OAc | 4-Br | 7-OMe | H |
| 207[1] | S | H | 2-OMe | 3-OAc | 4-Cl | 7-OMe | H |
| 208[1] | SO$_2$ | H | 2-OMe | 3-OH | 4-Br | 7-OMe | H |
| 209[1] | S | H | 2-OMe | 3-OAc | 7-OMe | 4-Br | H |
| 210[1] | S | H | 2-OMe | 3-OAc | 7-OMe | 4-Br | H |
| 211[1] | S | H | 2-OMe | 3-OBz | 7-OMe | 4-Br | H |
| 212[1] | S | Me | 2-OMe | 3-OMe | 7-OMe | 4-Br | H |
| 213[1] | S | H | 2-OMe | 3-OMe | 7-OMe | 4-Br | H |
| 214[1,2] | S | Ac | 2-OMe | 3-OAc | 7-OMe | 4-Br | H |
| 215[1,2] | S | Ac | 2-OMe | 3-OH | 7-OMe | 4-Br | H |
| 216[1] | S | Ac | 2-OMe | 3-OMe | 7-OMe | 4-Br | H |
| 217[1] | S | Me | 2-OMe | 3-OAc | 7-OMe | 4-Br | H |
| 218[1] | S | Me | 2-OMe | 3-OH | 7-OMe | 4-Br | H |
| 219[1] | SO$_2$ | H | 2-OMe | 3-OH | 7-OMe | 4-Br | H |
| 220[1] | SO$_2$ | H | 2-OMe | 3-OAc | 7-OMe | 4-Br | H |
| 221[1] | SO$_2$ | H | 2-OMe | 3-OAc | 7-OMe | 4-Br | H |
| 222[1] | SO | H | 2-OMe | 3-OAc | 7-OMe | 4-Br | H |
| 223[1] | SO | H | 2-OMe | 3-OAc | 7-OMe | 4-Br | H |
| 224 | S | H | 2-OMe | 3-OCO$_2$Me | 4-Br | 7-OMe | H |
| 225[1] | S | H | 2-OMe | 3-OCO$_2$Et | 4-Br | 7-OMe | H |
| 226[1,2] | S | H | 2-OMe | 3-OCO$_2$CH(Me)OAc | 4-Br | 7-OMe | H |
| 227[1] | S | H | 2-OMe | 3-OCO$_2$CH(Me)OAc | 4-Cl | 7-OMe | H |
| 228[1] | S | CO$_2$Me | 2-OMe | 3-OH | 4-Br | 7-OMe | H |
| 229[1] | S | CO$_2$Et | 2-OMe | 3-OH | 4-Br | 7-OMe | H |
| 230[1,2] | S | CO$_2$CH(Me)OAc | 2-OMe | 3-OH | 4-Br | 7-OMe | H |
| 231[1] | S | CO$_2$CH(Me)OAc | 2-OMe | 3-OH | 4-Cl | 7-OMe | H |
| 232[1] | S | CO$_2$CH(Me)OAc | 2-SMe | 3-OH | 4-F | 7-OMe | H |
| 233[1,2] | S | CO$_2$CH(Me)OAc | 2-OMe | 3-OAc | 4-Br | 7-OMe | H |
| 234[1] | S | CO$_2$CH(Me)OAc | 2-OMe | 3-OCO$_2$CH(Me)OAc | 4-Br | 7-OMe | H |
| 235[1,2] | O | Ac | 2-OMe | 3-OH | 4-Br | 7-OMe | H |
| 236[1,2] | O | Ac | 2-OMe | 3-OAc | 4-Br | 7-OMe | H |
| 237[1,2] | O | CO$_2$CH(Me)OAc | 2-OMe | 3-OH | 4-Br | 7-OMe | H |

TABLE I-continued

| Compound[a] | X | R[1] | R[2] | R[3] | R[4] | R[5] | T |
|---|---|---|---|---|---|---|---|
| 238[1] | O | CO$_2$CH(Me)OAc | 2-OMe | 3-OAc | 4-Br | 7-OMe | H |
| 239[1] | S | H | 2-OMe | 3-OH | 4-Br | 7-Me | H |
| 240[1] | S | H | 2-OMe | 3-OAc | 4-Br | 7-Me | H |
| 241[1] | S | H | 2-OMe | 3-OH | 4-Br | 7-F | H |
| 242[1] | S | H | 2-OMe | 3-OAc | 4-Br | 7-F | H |
| 243 | S | H | H | H | H | H | OCOEt |
| 244 | S | H | 2-Cl | 3-Cl | H | H | OCO—n-Pr |
| 245 | S | H | H | 4-Cl | H | H | COO—n-Bu |
| 246 | S | H | 1-Me | H | H | H | H |
| 247 | S | H | 2-CF$_3$ | H | H | H | H |
| 248 | S | H | 2-Et | H | H | H | H |
| 249 | S | H | H | 3-Cl | 7-OMe | H | H |
| 250 | S | H | H | 3-Cl | 7-Cl | H | H |
| 251 | S | H | H | 3-NO$_2$ | H | 7-NO$_2$ | H |
| 252 | S | H | 3-NMe$_2$ | H | H | 7-NMe$_2$ | H |
| 253 | S | H | 1-OH | H | H | H | H |
| 254 | S | H | 3-OAc | 7-F | H | H | H |
| 255 | S | H | 3-CH$_2$COMe | 4-Cl | H | H | H |
| 256 | S | H | 3-OCOCHMe$_2$ | H | 4-Cl | H | H |
| 257 | S | Ac | 3-OMe | 4-Cl | H | H | H |
| 258 | O | H | 2-CF$_3$ | H | H | H | H |
| 259 | S | Me | H | 3-OMe | H | 4-Cl | H |
| 260[1] | SO$_2$ | H | 4-Cl | 3-OH | H | H | H |
| 261 | S | Me | 7-F | 4-Cl | 3-OMe | H | H |
| 262 | S | Me | 3-OMe | 7-Me | H | H | H |
| 263 | S | Ac | 4-Cl | H | H | H | H |
| 264 | S | Ac | 3-OAc | 4-Cl | H | H | H |
| 265 | SO$_2$ | Ac | 4-Cl | H | H | H | 3-OH |
| 266 | SO$_2$ | Ac | 4-Cl | H | H | H | 3-OAc |
| 267[1] | SO$_2$ | Ac | 4-Br | H | H | H | 3-OAc |
| 268[1] | SO$_2$ | CO$_2$CH(Me)OAc | 4-Cl | H | H | H | 3-OH |
| 269[1] | SO$_2$ | H | 4-Cl | H | H | 3-OCO$_2$CH(Me)OAc | H |
| 270[1] | O | Ac | 4-Cl | H | H | H | 3-OAc |
| 271[1] | O | CO$_2$CH(Me)OAc | 4-Cl | H | H | H | 3-OH |
| 272[1] | O | CO$_2$CH(Me)OAc | 4-Cl | H | H | H | 3-OAc |
| 273[1] | O | H | 4-Cl | H | H | 3-OCO$_2$CH(Me)OAc | H |
| 274[1] | S | CH$_2$OAc | 4-Cl | H | H | H | 3-OAc |
| 275[1,2] | S | CH(Me)OAc | 4-Cl | H | H | H | 3-OAc |
| 276[1] | S | H | 2-OMe | 3-OH | 7-OH | H | H |
| 277[1] | S | H | 2-OMe | 3-OH | 7-OH | 4-Br | H |
| 278[1] | S | H | 2-OMe | 3-OAc | 7-OH | 4-Br | H |
| 279[1] | S | H | 2-OMe | 3-OAc | 7-OAc | 4-Br | H |
| 280[1] | S | Ac | 2-OMe | 3-OH | 7-OH | 4-Br | H |
| 281[1] | S | Ac | 2-OMe | 3-OAc | 7-OH | 4-Br | H |
| 282[1] | S | Ac | 2-OMe | 3-OAc | 7-OAc | 4-Br | H |
| 283[1,2] | S | Ac | 2-OMe | 3-OH | 7-OAc | 4-Br | H |
| 284[1,2] | SO$_2$ | Ac | 2-OMe | 3-OH | 4-Br | 7-OMe | H |
| 285[1] | SO$_2$ | CO$_2$CH(Me)OAc | 2-OMe | 3-OAc | 4-Br | 7-OMe | H |
| 286[1] | SO$_2$ | Ac | 2-OMe | 3-OCO$_2$COAc, Me (H) | 4-Br | 7-OMe | H |
| 287[1,2] | SO$_2$ | Ac | 2-OMe | 3-OAc | 4-Br | 7-OMe | H |
| 288[1,2] | SO$_2$ | CO$_2$CH(Me)OAc | 2-OMe | 3-OH | 4-Br | 7-OMe | H |
| 289[1,2] | S | Ac | 2-OEt | 3-OAc | 4-Cl | H | H |
| 290[1,2] | S | Ac | 2-OEt | 3-OH | 4-Cl | H | H |
| 291[1] | S | Me | H | 7-AC | H | H | 3-OMe |
| 292[1] | S | Me | H | H | 7-F | H | 3-OMe |
| 293[1] | S | Ac | H | H | 7-F | H | 3-OMe |
| 294[1] | S | Ac | H | H | 7-F | H | 3-OH |

[a]The symbol 1 next to the number of a compound indicates which compounds are preferred and the symbol 2 next to the number of a compound indicates which compounds are also more preferred.

The compounds of the Formula I have unexpected activity as inhibitors of the mammalian biosynthesis of both leukotrien B$_4$, as well as leukotrienes C$_4$, D$_4$, E$_4$ and F$_4$, the active elements of slow reacting substance of anaphylaxis (SRS-A). This inhibition of the biosynthesis of leukotrienes indicates that the compositions would be useful to treat, prevent or ameliorate, in mammals and especially in humans (1) pulmonary conditions including diseases such as asthma, (2) allergies and allergic reactions such as allergic rhinitis, contact dermatitis, allergic conjunctivitis and the like (3) inflammation such as arthritis, (4) pain, (5) skin conditions such as psoriasis and the like and (6) cardiovascular conditions such as angina and the like.

Representative compounds of Formula I have been tested using one or more of the following assays to determine their mammalian leukotriene biosynthesis inhibiting activity and other relevant activities.

Mouse Macrophase Assay

Mouse peritoneal macrophages were treated sequentially with arachidonic acid (labelled with tritium); the compound being evaluated as an inhibitor, and a stimulator (zymosan). Metabolites derived from arachidonic acid ($PGE_2$, 6-Keto $PG-F_{1@}$ and Leukotriene $C_4$) were separated from the incubation medium by extraction and chromatography, and then quantitated by determining the amount of radioactivity (cpm) associated with each of them. Inhibitors caused a reduction in the amount of radioactivity (cpm) associated with a given metabolite. (This protocol is identical to that described in the reference except that the radioactivity herein associated with the $LTC_4$ was determined by counting an aliquot of the final aqueous solution directly rather than chromatographing it first).

Reference: Humes J.L. et al.. J. Biol. Chem. 257. 1591–4 (1982).

Antigen Challenge 'in vitro' Assay

Male guinea pigs weighing 300–350 g were sensitized by injecting (i.p.) 0.5 ml of a suspension containing 0.4 mg of egg albumin (Ovalbumin, Grade V, Sigma Chemical Co.) and 4.0 g aluminum hydroxide in 19.6 ml of saline. Two weeks were permitted for sensitization to occur.

Three sensitized guinea pigs were stunned and exsanguinated. The tracheas were removed, freed of adhering tissue and divided longitudinally by cutting through the cartilaginous tissue directly opposite the muscle insertion. Each opened trachea was then transected between every second cartilage. Four of the cut sections were tied together, end to end in a series with No. 0.7 silk thread ensuring that the tracheal muscles were all in the same vertical plane. Thus, each chain consisted of tissue from three different animals.

The chain so formed was then suspended under 1 g of tension (by silk ties at each end) in a 20 ml organ bath containing 10 ml of modified[1] Krebs-Henseleit buffer solution gassed with 95% $O_2$ and 5% $CO_2$ at 37° C. Mepyramine (0.55 µg/ml) and indomethacin (2.67 µg/ml were added to the buffer to avoid the contribution of histamine receptors and cyclooxygenase products to the contraction. To record responses one end of the tracheal chain was attached to a Gould Statham UC-2 force displacement transducer which was connected to a Beckman Type R-dynograph. The preparations were allowed to equilibrate for one hour during which time the tissues were automatically washed (10 ml volume displacement) every 6 minutes.

[1] modified Krebs solution in grams/liter and (mM): NaCl-6.87 (120); glucose-2.1 (11); $NaHCO_3$-2.1 (25); KCl-0.32 (4.72); $CaCl_2$-0.28 (2.5); $MgSO_4.7H_2O$-0.11 (0.5); $KH_2PO_4$-0.16 (1.2); pH of bathing solution-7.35±0.05

After the equilibration period the tissues primed with methacholine (3 µg/lml; $1.5 \times 10^{-5}$M), washed and allowed to recover to baseline. The tissues were treated again with a second dose of methacholine, washed, allowed to return to baseline and washed for an additional hour.

Two chains were used as a control. These were incubated in a concentration of egg albumin sufficient to induce an average contraction of 50–80% of the methacholine response.

Each compound to be tested was added to two other baths (at a final concentration in each bath of 10 µg/ml or lower) 15 minutes prior to challenging the fresh chains with egg albumin.

The response of the challenged tissue was expressed as a percentage of the methacholine maximum. The % inhibition for each compound was then calculated. Compounds which at 10 µg/ml (final concentration) inhibited the egg albumin response by 50% or more were retested at a lower concentration.

RAT POLYMORPHONUCLEAR LEUKOCYTE (P.M.N.) Assay

Rats under ether anesthesia are injected (i.p.) with 8 ml of a suspension of sodium caseinate (6 grams in ca. 50 ml water). After 15–24 hours the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350× g, 5 min.), resuspended in buffer with vigorous shaking, filtered through lens paper, recentrifuged and finally suspended in buffer at a concentration of 10 cells/ml. A 500 µl aliquot of PMN suspension and test compound are preincubated for 2 minutes at 37° C., followed by the addition of 10 µM A-23187. The suspension is stirred for an additional 4 minutes then bioassayed for $LTB_4$ content by adding an aliquot to a second 500 µl portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Results from the assays described above for several compounds of Formula I are shown in Table II.

TABLE II

| | | ASSAY RESULTS | | |
|---|---|---|---|---|
| Compound | | Macrophage IC$_{50}$ (μg/ml) | P.M.N. IC$_{50}$ (μg/ml) | In Vitro Antigen Challenge % Inhibiton at concentration in parenthesis (μg/ml) |
| 1 | phenothiazine (H-N, S bridging two phenyl rings) | 0.06 | 0.4 | 100% (10) |
| 2 | phenothiazine with Cl, Cl substituents | 0.04 | — | — |
| 3 | phenothiazine with Cl substituent | 0.01–0.1 | 0.05–0.5 | 37% (10) |
| 4 | phenothiazine with CH$_3$ substituent | 5 | — | 76% (10) |
| 5 | phenothiazine with CF$_3$ substituent | 0.1 | — | 7% (10) |
| 6 | phenothiazine with OH substituent | 0.1–1 | 0.016 | 100 (10)<br>47 (1) |
| 7 | phenothiazine with OAc substituent | 0.01–0.1 | 0.005 | 60 (10) |
| 8 | phenothiazine with COCH$_3$ substituent | 0.2 | — | 60 (10) |

TABLE II-continued

ASSAY RESULTS

| Compound | | Macrophage IC$_{50}$ (μg/ml) | P.M.N. IC$_{50}$ (μg/ml) | In Vitro Antigen Challenge % Inhibiton at concentration in parenthesis (μg/ml) |
|---|---|---|---|---|
| 9 | [Diphenylamine with S bridge, OH and Cl substituents] | — | 0.005 | 97 (3) |
| 10 | [Diphenylamine with S bridge, OTs and Cl substituents] | — | 0.1–1 | 14 (3) |
| 11 | [Diphenylamine with S bridge, OAc and Cl substituents] | 0.1 | 92%[1] | 100 (10) 62 (1) |
| 12 | [Diphenylamine with S bridge, OMe and Cl substituents] | — | 0.01–0.1 | 60 (1) |
| 13 | [Diphenylamine with S bridge, MeO and Cl substituents] | 0.12 | — | 22 (10) |
| 14 | [Diphenylamine with S bridge, two Cl substituents] | 0.01–0.1 | 0.005–0.05 | 1 (10) |
| 15 | [Diphenylamine with S bridge, two NO$_2$ substituents] | 0.0016–0.008 | — | 21 (10) |

TABLE II-continued

ASSAY RESULTS

| Compound | Macrophage IC$_{50}$ (μg/ml) | P.M.N. IC$_{50}$ (μg/ml) | In Vitro Antigen Challenge % Inhibiton at concentration in parenthesis (μg/ml) |
|---|---|---|---|
| 16 (MeO-phenyl-NH-phenyl-S- with OMe, OH, Br substituents) | — | 0.01 | — |
| 17 ((Me)$_2$N-phenyl-NH-phenyl-S-N(Me)$_2$) | 5 | — | — |
| 18 (phenyl-NH-phenyl-S- with OH) | — | 0.05–0.5 | 3 (10) |
| 19 (F-phenyl-NH-phenyl-S- with OAc) | — | 0.005 | — |
| 20 (phenyl-NH-phenyl-S- with Cl and OC(O)CH(Me)$_2$) | — | 0.005–0.05 | 65 (10) |
| 21 (phenyl-N(Ac)-phenyl-S-) | 5 | — | — |
| 22 (phenyl-N(Ac)-phenyl-S- with Cl, OMe) | 1.0 | 1.0 | 91 (10) |

TABLE II-continued

| Compound | ASSAY RESULTS Macrophage IC$_{50}$ ($\mu$g/ml) | P.M.N. IC$_{50}$ ($\mu$g/ml) | In Vitro Antigen Challenge % Inhibiton at concentration in parenthesis ($\mu$g/ml) |
|---|---|---|---|
| 23 (diphenyl ether with NH bridge, CF$_3$ substituent) | — | 0.05–0.5 | 40 (3) |
| 24 (diphenyl ether with NH bridge) | 0.1 | 5 | 88% (1) |
| 25 (Cl, Me-N, S-linked diphenyl with OAc) | — | 0.5 | 1–9% (3) |
| 26 (Me-N, S-linked diphenyl with OMe, Cl) | 1 | 5 | 3% (10) |
| 27 (Me-N, S-linked diphenyl with isobutyryloxy, Cl) | — | 0.005–0.05 | 6% (3) |

[1]Percentage inhibition at 5 $\mu$g/ml.

In addition to the assay results described in Table II, the following assays were employed to determine the effectiveness of selected compounds of Formula I as antiasthma and analgesia agents.

Asthmatic Rat Assay

Rats were obtained from an inbred line of asthmatic rats. Both female and male rats from 200 to 300 g were used.

Egg albumin (EA), grade V, crystallized and lyophilized, was obtained from Sigma Chemical Co., St. Louis. *Bordetella pertussis* vaccine, containing 30×10$^9$ killed bacteria per ml was obtained from the Institut Armand-Frappier, Laval des Rapides, Quebec. Aluminum hydroxide was obtained from the Regeis Chemical Company, Chicago.

The challenge and subsequent respiratory recordings were carried out in a clear plastic box with internal dimensions 10×6×4 inches. The top of the box was removable; in use, it was held firmly in place by four clamps and an airtight seal was maintained by a soft rubber gasket. Through the center of each end of the chamber a Devilbiss nebulizer (No. 40) was inserted via an airtight seal and each end of the box also had an outlet. A Fleisch No. 0000 pneumotachograph was inserted into one end of the box and coupled to a Grass volumetric pressure transducer (PT5-A) which was then connected to a Beckman Type R Dynograph through appropriate couplers. While aerosolizing the antigen, the outlets were open and the pneumotachograph was isolated from the chamber. The outlets were closed and the pneumotachograph and the chamber were connected during the recording or the respiratory patterns. For challenge, 2 ml of a 3% solution of antigen in saline was placed into each nebulizer and the aerosol was generated with air from a small potter diaphragm pump operating at 10 psi and a flow of 8 liters/minutes.

Rats were sensitized by injecting (s.c.) 1 ml of a suspension containing 1 mg EA and 200 mg aluminum hydroxide in saline. Simultaneously, they received a injection (i.p.) of 0.5 ml of *B. pertussis* vaccine. They were used between days 14 and 18 postsensitization. In order to eliminate the serotonin component of the response, rats were pretreated intravenously 5 minutes prior to aerosol challenge with 30 gm kg$^{-1}$ methylserzide. Rats were then exposed to an aerosol of 3% EA in saline for exactly 1 minute, then their respiratory profiles were recorded for a further 25-30 minutes. The duration of continuous dyspnoea was measured from the respiratory recordings.

Compounds were generally administered either intraperitoneally 1 hour prior to challenge or orally 1½ hours prior to challenge. They were either dissolved in dimethylsulfoxide or suspended in 0.1% methocel and 0.5% Tween 80. The volume injected has 2 ml kg−1 (intraperitoneally) or 10 ml kg−1 (orally). Prior to oral treatment rats were starved overnight. Their activity was determined in terms of their ability to decrease the duration of symptoms of dyspnoea in comparison with a group of vehicle-treated controls. Usually, a compound was evaluated at a series of doses and an ED$_{50}$ was determined. This was defined as the dose (mg/kg) which would inhibit the duration of symptoms by 50%.

PAF-Induced Hyperalgesia Assay

Female Sprague-Dawley rats, 35-40 g were fasted overnight. Platelet activating factor, PAF, (L-lecithin B-acetyl O-alkyl) 1 μg/0.1 ml was given by subplantar injection in the rat paw. The compounds to be evaluated were homogenized in aqueous Vehicle (0.9% benzyl alcohol, 0.5% Tween 80 and 0.4% methylcellulose) and administered orally in a volume of 0.1 ml, 30 minutes prior to PAF.

Animals were tested 1, 2, 3 and 4 hours after PAF administration. The vocalization threshold, defined as the pressure (mm Hg) needed to evoke a squeak response, was recorded for both the injected and contralateral paw. No animal was subjected to pressure greater than 60 mm Hg. Hyperalgesia is defined as a decrease in vocalization threshold as compared to a normal paw. Percent inhibition of hyperalgesia was calculated as the proportion of animals with vocalization thresholds greater than 200% of controls.

Results for the assays described above for several compounds of Formula I are shown in Table III.

TABLE III
ASSAY RESULTS

| Compound | Asthmatic Rat Assay % inhibition and dose | PAF Induced Hyperalgesia Assay % inhibition and dose |
|---|---|---|
| [structure: Ph-N(H)-S-Ph] | 53% (0.5 mg kg$^{-1}$ p.o.) | 50% (3 mg kg$^{-1}$ p.o.) |
| [structure: Ph-N(H)-SO$_2$-Ph-OH] | 70% (3 mg kg$^{-1}$ p.o.) | 60% (3 mg kg$^{-1}$ p.o.) |
| [structure: Ph-N(H)-SO$_2$-Ph(Cl)-OH] | 59% (1.5 mg kg$^{-1}$ p.o.) | 50% (1.2 mg kg$^{-1}$ p.o.) |
| [structure: Ph-N(Me)-S-Ph(Cl)-OMe] | 50% (0.2 mg kg$^{-1}$ p.o.) | 50% (0.016 mg kg$^{-1}$ p.o.) |

TABLE III-continued

ASSAY RESULTS

| Compound | Asthmatic Rat Assay % inhibition and dose | PAF Induced Hyperalgesia Assay % inhibition and dose |
|---|---|---|
| 4-F, 2-Me-C₆H₃-N(Me)-S-C₆H₂(2-Me)(3-Cl)(4-OMe) | 42% (3 mg kg⁻¹ p.o.) | — |
| 2-Me-C₆H₄-N(Me)-S-C₆H₂(3-Me)(5-Cl)(4-OC(O)CH(Me)₂) | 35% (3 mg kg⁻¹ p.o.) | 70% (1 mg kg⁻¹ p.o.) |
| 2,4-Me₂-C₆H₃-N(Me)-S-C₆H₃(2-Me)(4-OMe) | 58% (3 mg kg⁻¹ p.o.) | 30% (1 mg kg⁻¹ p.o.) |
| 2-Me-C₆H₄-NH-S(=O)-C₆H₂(2-Me)(3-Cl)(4-OMe) | 56% (3 mg kg⁻¹ p.o.) | — |
| 2-Me-C₆H₄-NH-SO₂-C₆H₂(2-Me)(3-OH)(4-OH) | 65% (1.5 mg kg⁻¹ p.o.) | — |
| 2-Me-C₆H₄-N(Ac)-S-C₆H₂(2-Me)(3-Cl)(4-OMe) | 59% (1.5 mg kg⁻¹ p.o.) | 50% (0.01 mg kg⁻¹ p.o.) |
| 2-Me-C₆H₄-N(Ac)-S-C₆H₂(2-Me)(3-Cl)(4-OH) | 61% (3 mg kg⁻¹ p.o.) | — |

TABLE III-continued

ASSAY RESULTS

| Compound | Asthmatic Rat Assay % inhibition and dose | PAF Induced Hyperalgesia Assay % inhibition and dose |
|---|---|---|
| (Ph-Ac-N-Ph, S, Cl, OAc) | 58% (3 mg kg$^{-1}$ p.o.) | — |
| (F-Ph-Ac-N-Ph, S, Cl, OMe) | 36% (3 mg kg$^{-1}$ p.o.) | — |
| (F-Ph-Me-N-Ph, S=O, Cl, OMe) | 52% (3 mg kg$^{-1}$ p.o.) | — |
| (Ph-H-N-Ph, O) | 51% (1.5 mg kg$^{-1}$ p.o.) | — |
| (Ph-Me-N-Ph, O, Cl, OMe) | 49% (0.3 mg kg$^{-1}$ p.o.) | — |
| (MeO-Ph-Ac-N-Ph, S, Br, OMe, OAc) | 58% (0.5 mg Kg$^{-1}$ p.o.) | 60% (0.03 mg Kg$^{-1}$ p.o.) |

TABLE III-continued

ASSAY RESULTS

| Compound | Asthmatic Rat Assay % inhibition and dose | PAF Induced Hyperalgesia Assay % inhibition and dose |
|---|---|---|
| MeO-C6H3(Me)-S-C6H2(Br)(OH)(OMe) with N(Ac) substituent | 78% (1.5 mg Kg$^{-1}$ p.o.) | 60% (0.1 mg Kg$^{-1}$ p.o.) |
| MeO-C6H3(Me)-S-C6H2(Br)(OH)(OMe) with N-CH(CH3)(CO2)(OAc) substituent | 42% (5.0 mg Kg$^{-1}$ p.o.) | 60% (3.0 mg Kg$^{-1}$ p.o.) |

The cytoprotective activity of a compound may be observed in both animals and man by noting the increased resistance of the gastrointestinal mucosa to the noxious effects of strong irritants, for example, the ulcerogenic effects of aspirin or indomenthacin. In addition to lessening the effect of non-steroidal anit-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced gastric ulcer assay and (B) an indomethacin-induced ulcer assay.

A. Ethanol-Induced Gastric Ulcer

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The pharmaceutical compositions will contain a sufficient amount of a compound of Formula I in a dosage form suitable for inhibiting the mammalian biosynthesis of leukotrienes or, for the treatment desired. The effective concentration of a Formula I compound in the composition will vary as required by the nature and the severity of the condition to be treated, the particular compound selected, the mode of administration, the dosage form and the pharmacological effect and level desired.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

A general daily dosage of a Formula I compound for anti-asthmatic, anti-allergic, anti-inflammatory and, generally, uses other than cytoprotection will range from about 10 μg/kg to 20 mg/kg of body weight. A preferred daily dosage range is from 50 μg/kg to 20 mg/kg and a most preferred dosage range is from 100 μg/kg to 10 mg/kg.

The exact amount of a compound of the Formula I to be used as a cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug (for example, indomethacin) that might otherwise cause such damage. For such use, the compound of Formula I is administered from 30 minutes prior up to 30 minutes after administration of the NSAID. Preferably, it is administered prior to or simultaneously with the NSAID.

The effective daily dosage level for compounds of Formula I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, $N,N^1$-dibenzylethylenediamine, morpholine, N-ethyl morpholine, polyamine resins and the like.

When the compound of Formula I is basic, salts may be prepared from pharmaceutically acceptable non-toxic acids, including inorganic and organic acids. Such acids include hydrochloric, hydrobromic, sulfuric, nitric, isethionic, methanesulfonic, ethanesulfonic, benzenesulfonic, p-toluenesulfonic, acetic, benzoic, camphorsulfonic, citric, fumaric, gluconic, glutamic, lactic, malic, maleic, mandelic, mucic, pamoic, pantothenic, phosphoric, succinic, tartaric acid and the like. Particularly preferred are hydrochloric, hydrobromic, citric, maleic, phosphoric, sulfuric and tartaric acids. For a helpful discussion of pharmaceutical salts see S. M. Berge et al., Journal of Pharmaceutical Sciences, 66, 1-19 (1977), the disclosure of which is hereby incorporated herein by reference.

The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being trated and on the nature of the active ingredient. They may be conveniently presented in unit dosage form and prepared by any of the methods well-known in the art of pharmacy.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 μg to about 200 μg, administered as needed.

For treating allergies or allergic reactions, such as allergic conjunctivitis, allergic rhinitis and the like, the Formula I compound may be administered by any conventional mode, e.g. orally, parenterally, topically, subcutaneously, by inhalation and the like.

The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight of the active ingredient (Formula I compound) may vary from about 0.001 to about 10%.

For treating inflammation the mode of administration may be oral, parenteral, by suppository and the like. The various dosage forms are the same as those described above.

For treating skin diseases such as psoriasis, atopic dermatitis and the like, oral, topical or parenteral administration is useful. For topical application to the diseased area salves, patches, controlled release patches, emulsions, etc., are convenient dosage forms.

For use as an analgesic, i.e. for treating pain, any suitable mode of administration may be used, e.g., oral, parenteral, by insufflation, by suppository and the like.

For treating cardiovascular conditions such as angina pectoris, etc., any suitable mode of administration, e.g. oral, parenteral, topical, insufflation, etc. and dosage form e.g. pills, liquid formulations, controlled release capsules, controlled release skin patches, etc. may be used.

In addition to the common dosage forms set out above, the compound of Formula I may also be administered for the various utilities and indications or for inhibiting leukotriene synthesis by controlled release means and/or delivery devices such as those described in U.S. Pat. Nos. 3,845,770; 3,916,899; 3,536,809; 3,598,123; 3,630,200 and 4,008,719. Dosage forms for application to treat the eye are also disclosed in U.S. 4,348,398. These disclosures are hereby incorporated herein by reference For use where a composition for intravenous administration is employed, a suitable dosage range for anti-asthmatic, anti-inflammatory or anti-allergic use is from about 0.01 mg to about 20 mg (preferably from about 0.1 mg to about 10 mg) of a compound of formula I per kg of body weight per day and for cytoprotective use from about 0.002 mg to about 100 mg (preferably from about 0.02 mg to about 30 mg and more preferably from about 0.1 mg to about 10 mg) of a compound of Formula I per kg of body weight per day. In the case where an oral composition is employed, a suitable dosage range for anti-asthmatic, anti-inflammatory or anti-allergic use is, e.g. from about 1 to about 100 of a compound of formula I per kg of body weight per day, preferably from about 5 mg to about 40 mg per kg and for cytoprotective use from about 0.01 mg to about 100 mg (preferably from about 0.1 mg to about 30 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene inhibitors of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the leukotriene inhibitors of Formula I:

| Injectable Suspension | mg/ml |
| --- | --- |
| Compound of Formula I | 2 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Tablet | mg/tablet |
| --- | --- |
| Compound of Formula I | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |

-continued

| | 600 |
| --- | --- |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, almino-profen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$NA$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

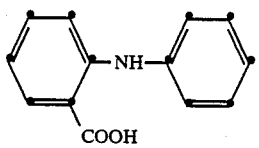

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

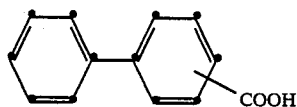

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

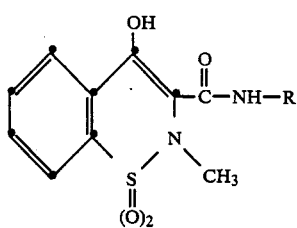

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITCl, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain other inhibitors of the biosynthesis of the leukotrienes such as are disclosed in pending U.S. patent applications Ser. No. 539,342, filed Oct. 5, 1983, Ser. No. 459,924, filed Jan. 21, 1983, Ser. No. 539,215, filed Oct. 5, 1983, and Ser. No. 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an H$_1$ or H$_2$-receptor antagonist, such as for instance cimetidine, ranitidine, terfenadine, famotidine, aminothiadiazoles disclosed in EP 81102976.8 and like compounds, such as those disclosed in U.S. Pat. Nos. 4,283,408; 4,362,736; 4,394,508; European Patent Application No. 40,696 and a pending application, U.S. Ser. No. 301,616, filed Sept. 14, 1981.

The pharmaceutical compositions may also contain a K+/H+ ATPase inhibitor such as omeprazole, disclosed in U.S. Pat. No. 4,255,431, and the like. Each of the references referred to in this paragraph is hereby incorporated herein by reference.

Another embodiment of the present invention are the novel compounds encompassed by Formula I and the pharmaceutically acceptable salts thereof. These novel compounds are indicated in Table IV.

TABLE IV
NOVEL COMPOUNDS OF FORMULA I

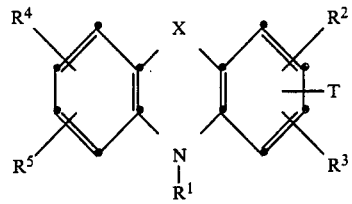

| Compound[a] | X | $R^1$ | $R^2$ | $R^3$ | $R^4$ | $R^5$ | T |
|---|---|---|---|---|---|---|---|
| 1 | S | H | 4-Cl | H | H | H | 3-OH |
| 2 | S | H | 4-Cl | H | H | H | 3-OAc |
| 3[1] | S | Me | 4-Cl | H | H | H | 3-OMe |
| 4 | S | Ac | 4-Cl | H | H | H | 3-OMe |
| 5 | S | H | 4-Cl | H | H | H | 3-OBz |
| 6 | S | H | 4-Cl | H | H | H | 3-OCOCH(Me)$_2$ |
| 7 | S | Me | 4-Cl | H | H | H | 3-OCOCH(Me)$_2$ |
| 8[1] | S | Ac | 4-Cl | H | H | H | 3-OAc |
| 9[1] | S | Ac | 4-Cl | H | H | H | 3-OH |
| 10 | SO$_2$ | Me | 4-Cl | H | H | H | 3-OMe |
| 11 | SO | Me | 4-Cl | H | H | H | 3-OMe |
| 12 | S | Me | H | 7-Ac | H | H | 3-OMe |
| 13 | O | Me | 4-Cl | H | H | H | 3-OAc |
| 14 | S | Me | 4-Cl | H | H | H | 3-OAc |
| 15 | S | Me | H | H | 7-F | H | 3-OMe |
| 16 | S | Ac | H | H | 7-F | H | 3-OMe |
| 17 | S | Ac | H | H | 7-F | H | 3-OH |
| 18 | S | Ac | H | H | 7-F | H | 3-OAc |
| 19 | S | Me | H | H | 7-Me | H | 3-OMe |
| 20 | S | H | H | H | 7-F | H | 3-OAc |
| 21 | S | Me | H | H | 9-Cl | H | 3-OMe |
| 22 | S | Me | H | H | 9-Cl | H | 3-OAc |
| 23 | S | Me | H | H | 7-Me | H | 3-OAc |
| 24 | S | H | H | H | 9-Cl | H | 3-OAc |
| 25 | S | H | H | 4-CF$_3$ | H | H | 3-OAc |
| 26 | S | H | H | 4-Cl | H | H | 3-OTs |
| 27 | S | Ac | H | 4-Cl | 7-F | H | 3-OMe |
| 28 | S | Ac | H | 4-Cl | 7-F | H | 3-OH |
| 29 | S | Me | H | 4-Cl | 7-F | H | 3-OMe |
| 30 | S | H | H | 2-OEt | 4-Cl | H | 3-OH |
| 31 | SO | H | H | H | H | H | 3-OAc |
| 32[1] | SO$_2$ | H | H | H | H | H | 3-OAc |
| 33[1] | SO$_2$ | H | H | 4-Cl | H | H | 3-OAc |
| 34[1] | SO$_2$ | H | H | 4-Cl | H | H | 3-OH |
| 35 | SO$_2$ | H | H | H | H | H | 3-OH |
| 36 | SO$_2$ | H | H | H | 7-F | H | 3-OAc |
| 37 | SO$_2$ | H | H | 4-Cl | H | H | 3-OTs |
| 38 | SO$_2$ | H | H | 4-OH | H | H | 3-OH |
| 39 | S | H | 1-OMe | 2-OMe | 4-Me | H | 3-OH |
| 40 | S | H | 1-OMe | 2-OMe | 4-Me | H | 3-OAc |
| 41[1] | SO$_2$ | H | 1-OMe | 2-OMe | 4-Me | H | 3-OH |
| 42 | SO$_2$ | H | 4-OMe | H | H | H | 3-OH |
| 43 | S | H | 1-OH | 2-C(Me)$_3$ | H | 4-C(Me)$_3$ | H |
| 44 | SO$_2$ | H | 1-Cl | H | H | H | 3-OH |
| 45 | SO$_2$ | Ac | 1-Cl | H | H | H | 3-OH |
| 46 | SO$_2$ | Ac | 1-Cl | H | H | H | 3-OAc |
| 47 | S | Me | 1-Cl | H | H | H | 3-OAc |
| 48 | S | Me | 1-Cl | H | H | H | 3-OH |
| 49 | SO | H | 1-OMe | 2-OMe | 4-Me | H | 3-OH |
| 50 | SO | H | 1-OMe | 2-OMe | 4-Me | H | 3-OAc |
| 51 | SO$_2$ | H | 1-OMe | 2-OMe | 4-Me | H | 3-OAc |
| 52[1] | S | H | 2-OMe | 3-OH | 4-Br | 7-OMe | H |
| 53[1] | S | H | 2-OMe | 3-OH | 4-Cl | 7-OMe | H |
| 54[1] | S | H | 2-OMe | 3-OAc | 4-Br | 7-OMe | H |
| 55 | S | H | 2-OMe | 3-OAc | 4-Cl | 7-OMe | H |
| 56 | SO$_2$ | H | 2-OMe | 3-OH | 4-Br | 7-OMe | H |
| 57 | SO$_2$ | H | H | 3-OH | H | 7-F | H |
| 58 | SO$_2$ | H | 2-OMe | 3-OAc | 4-Br | 7-OMe | H |
| 59[1] | O | Ac | 2-OMe | 3-OH | 4-Br | 7-OMe | H |
| 60[1] | O | Ac | 2-OMe | 3-OAc | 4-Br | 7-OMe | H |
| 61[1] | O | CO$_2$CH(Me)OAc | 2-OMe | 3-OH | 4-Br | 7-OMe | H |
| 62 | O | CO$_2$CH(Me)OAc | 2-OMe | 3-OAc | 4-Br | 7-OMe | H |
| 63 | S | H | 2-OMe | 3-OH | 4-Br | 7-Me | H |

TABLE IV-continued

NOVEL COMPOUNDS OF FORMULA I

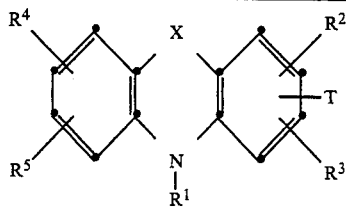

| Compound[a] | X | R[1] | R[2] | R[3] | R[4] | R[5] | T |
|---|---|---|---|---|---|---|---|
| 64 | S | H | 2-OMe | 3-OAc | 4-Br | 7-Me | H |
| 65 | S | H | 2-OMe | 3-OH | 4-Br | 7-F | H |
| 66 | S | H | 2-OMe | 3-OAc | 4-Br | 7-F | H |
| 67 | SO | H | 2-OMe | 3-OAc | 4-Br | 7-OMe | H |
| 68 | SO$_2$ | H | 2-OMe | 3-OH | H | 7-OMe | H |
| 69 | SO$_2$ | H | 2-OMe | 3-OAc | H | 7-OMe | H |
| 70[1,2] | S | Ac | 2-OMe | 4-Br | 7-OMe | H | 3-OAc |
| 71[1,2] | S | Ac | 2-OMe | 4-Cl | 7-OMe | H | 3-OAc |
| 72 | S | Ac | 2-OMe | 4-F | 7-OMe | H | 3-OAc |
| 73 | S | Ac | 2-OMe | 4-I | 7-OMe | H | 3-OAc |
| 74 | S | Ac | 2-OMe | 4-CF$_3$ | 7-OMe | H | 3-OAc |
| 75 | S | Ac | 2-OMe | 4-CN | 7-OMe | H | 3-OAc |
| 76 | S | Ac | 2-OEt | 4-Br | 7-OEt | H | 3-OAc |
| 77 | S | Ac | 2-OEt | 4-Cl | 7-OEt | H | 3-OAc |
| 78 | S | Ac | 2-OMe | 4-Br | 7-OEt | H | 3-OAc |
| 79 | S | Ac | 2-OMe | 4-Cl | 7-OEt | H | 3-OAc |
| 80 | S | Ac | 2-OMe | 4-F | 7-OEt | H | 3-OAc |
| 81 | S | Ac | 2-OEt | 4-Br | 7-OMe | H | 3-OAc |
| 82 | S | Ac | 2-OEt | 4-Cl | 7-OMe | H | 3-OAc |
| 83 | S | Ac | 2-OEt | 4-F | 7-OMe | H | 3-OAc |
| 84 | S | Ac | 2-OEt | 4-CF$_3$ | 7-OMe | H | 3-OAc |
| 85 | S | H | 2-OMe | 4-Br | 7-OMe | H | 3-OH |
| 86 | S | H | 2-OMe | 4-Cl | 7-OMe | H | 3-OH |
| 87[1] | S | H | 2-OMe | 4-F | 7-OMe | H | 3-OH |
| 88[1] | S | H | 2-OMe | 4-CF$_3$ | 7-OMe | H | 3-OH |
| 89 | S | H | 2-OMe | 4-Br | 7-OMe | H | 3-OAc |
| 90[1] | S | H | 2-OMe | 4-Br | 7-OMe | H | 3-OBz |
| 91[1] | S | H | 2-OMe | 4-Br | 7-OMe | H | 3-OCOCHMe$_2$ |
| 92[1] | S | H | 2-OMe | 4-Br | 7-OMe | 3-OCH$_2$CO$_2$H | H |
| 93[1] | S | Ac | 2-OMe | 4-Br | 7-OMe | H | 3-OBz |
| 94[1] | S | Ac | 2-OMe | 4-Br | 7-OMe | H | 3-OMe |
| 95[1] | S | Ac | 2-OMe | 4-Br | 7-OMe | 3-OCH$_2$CO$_2$H | H |
| 96[1] | S | Ac | 2-OMe | 4-Cl | 7-OMe | 3-OCH$_2$CO$_2$H | H |
| 97[1] | S | CH$_2$OAc | 2-OMe | 4-Br | 7-OMe | H | 3-OH |
| 98[1] | S | CH$_2$OAc | 2-OMe | 4-Cl | 7-OMe | H | 3-OH |
| 99[1] | S | CH$_2$OAc | 2-OMe | 4-Br | 7-OMe | H | 3-OAc |
| 100[1] | S | CH$_2$OAc | 2-OMe | 4-Br | 7-OMe | H | 3-OBz |
| 101[1] | S | CH$_2$OAc | 2-OMe | 4-Br | 7-OMe | H | 3-OMe |
| 102[1] | S | CH$_3$ | 2-OMe | 4-Br | 7-OMe | H | 3-OH |
| 103[1] | S | CH$_3$ | 2-OMe | 4-Br | 7-OMe | H | 3-OAc |
| 104[1] | S | CH$_3$ | 2-OMe | 4-Cl | 7-OMe | H | 3-OH |
| 105[1] | S | Me | 2-OMe | 4-F | 7-OMe | H | 3-OH |
| 106[1] | S | Me | 2-OMe | 4-CF$_3$ | 7-OMe | H | 3-OH |
| 107[1] | S | CH(Me)OAc | 2-OMe | 4-Br | 7-OMe | H | 3-OH |
| 108[1] | S | CH(Me)OCOC(Me)$_3$ | 2-OMe | 4-Br | 7-OMe | H | 3-OH |
| 109[1] | S | CH(Me)OAc | 2-OMe | 4-Cl | 7-OMe | H | 3-OH |
| 110[1] | S | CH(Me)OAc | 2-OMe | 4-F | 7-OMe | H | 3-OH |
| 111[1] | S | CH(Me)OAc | 2-OMe | 4-CF$_3$ | 7-OMe | H | 3-OH |
| 112 | S | H | 2-OMe | 4-Br | 7-OMe | 3-OCO$_2$Me | H |
| 113 | S | H | 2-OMe | 4-Br | 7-OMe | 3-OCO$_2$Et | H |
| 114[1] | S | H | 2-OMe | 4-Br | 7-OMe | 3-OCO$_2$CH(Me)OAc | H |
| 115 | S | H | 2-OMe | 4-Cl | 7-OMe | 2-OCO$_2$CH(Me)OAc | H |
| 116 | S | CO$_2$Me | 2-OMe | 4-Br | 7-OMe | H | 3-OH |
| 117 | S | CO$_2$Et | 2-OMe | 4-Br | 7-OMe | H | 3-OH |
| 118[1,2] | S | CO$_2$CH(Me)OAc | 2-OMe | 4-Br | 7-OMe | H | 3-OH |
| 119[1,2] | S | CO$_2$CH(Me)OAc | 2-OMe | 4-Cl | 7-OMe | H | 3-OH |
| 120 | S | CO$_2$CH(Me)OAc | 2-OMe | 4-F | 7-OMe | H | 3-OH |
| 121[1,2] | S | CO$_2$CH(Me)OAc | 2-OMe | 4-Br | 7-OMe | H | 3-OAc |
| 122 | S | CO$_2$CH(Me)OAc | 2-OMe | 4-Br | 7-OMe | 3-OCO$_2$CH(Me)OAc | H |
| 123[1,2] | S | Ac | 2-OMe | 4-Br | 7-OMe | H | 3-OH |
| 124 | S | Ac | 2-OMe | 4-Cl | 7-OMe | H | 3-OH |
| 125 | S | Me | 2-OMe | 4-Br | 7-OMe | H | 3-OMe |
| 126 | S | H | 2-OMe | 4-Br | 7-OMe | H | 3-OMe |
| 127[1] | S | CH(Me)OAc | 4-Cl | H | H | H | 3-OAc |
| 128[1] | SO$_2$ | Ac | 4-Cl | H | H | H | 3-OH |
| 129[1] | SO$_2$ | Ac | 4-Cl | H | H | H | 3-OAc |
| 130[1] | S | Ac | 2-OEt | 4-Cl | H | H | 3-OH |
| 131[1] | S | Ac | 2-OEt | 4-Cl | H | H | 3-OAc |
| 132[1] | S | Ac | 2-OMe | 4-Br | 7-OH | H | 3-OH |

TABLE IV-continued

NOVEL COMPOUNDS OF FORMULA I

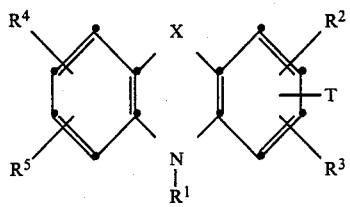

| Compound[a] | X | R[1] | R[2] | R[3] | R[4] | R[5] | T |
|---|---|---|---|---|---|---|---|
| 133[1] | S | Ac | 2-OMe | 4-Br | 7-OAc | H | 3-OH |
| 134[1] | SO₂ | Ac | 2-OMe | 4-Br | 7-OMe | H | 3-OH |
| 135[1] | SO₂ | Ac | 2-OMe | 4-Br | 7-OMe | H | 3-OAc |
| 136[1] | SO₂ | CO₂CH(Me)OAc | 2-OMe | 4-Br | 7-OMe | H | 3-OH |
| 137[1,2] | S | CO₂CHOCO<br>   \|     \|<br>  Me  C(Me)₃ | H | 4-Br | 7-OMe | 2-OMe | 3-OH |

[a]The symbol 1 next to the number of a novel compound indicates which compounds are preferred and the symbol 2 next to the number of a novel compound indicates which compounds are also more preferred.

Some of the compounds described herein contain one or more centers of asymmetry and may thus give rise to diastereoisomers and optical isomers. The present invention is meant to comprehend such possible diastereoisomers as well as their racemic and resolved, optically active forms.

Scheme I, below, illustrates the preparation of compounds of the formula I.

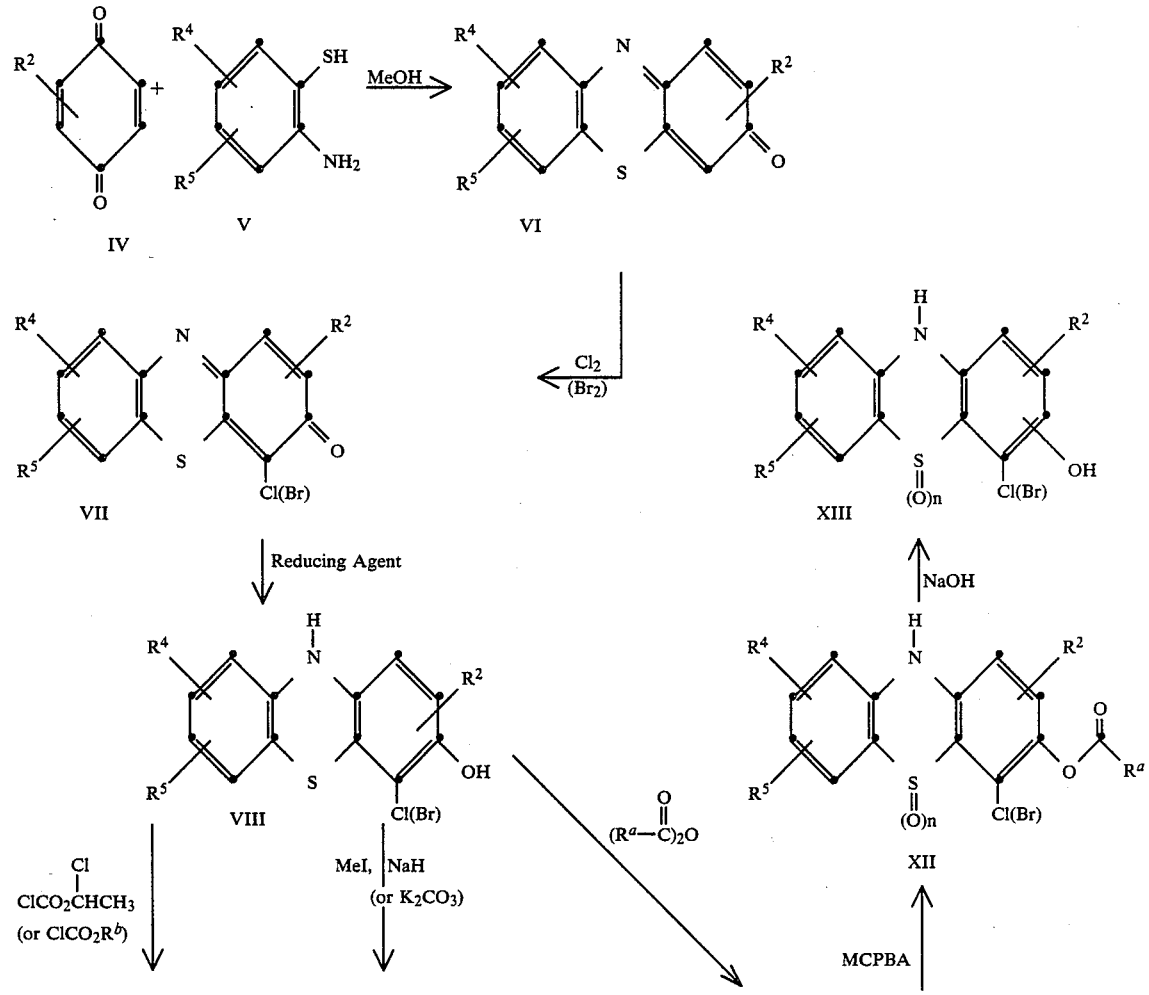

SCHEME I

-continued
SCHEME I

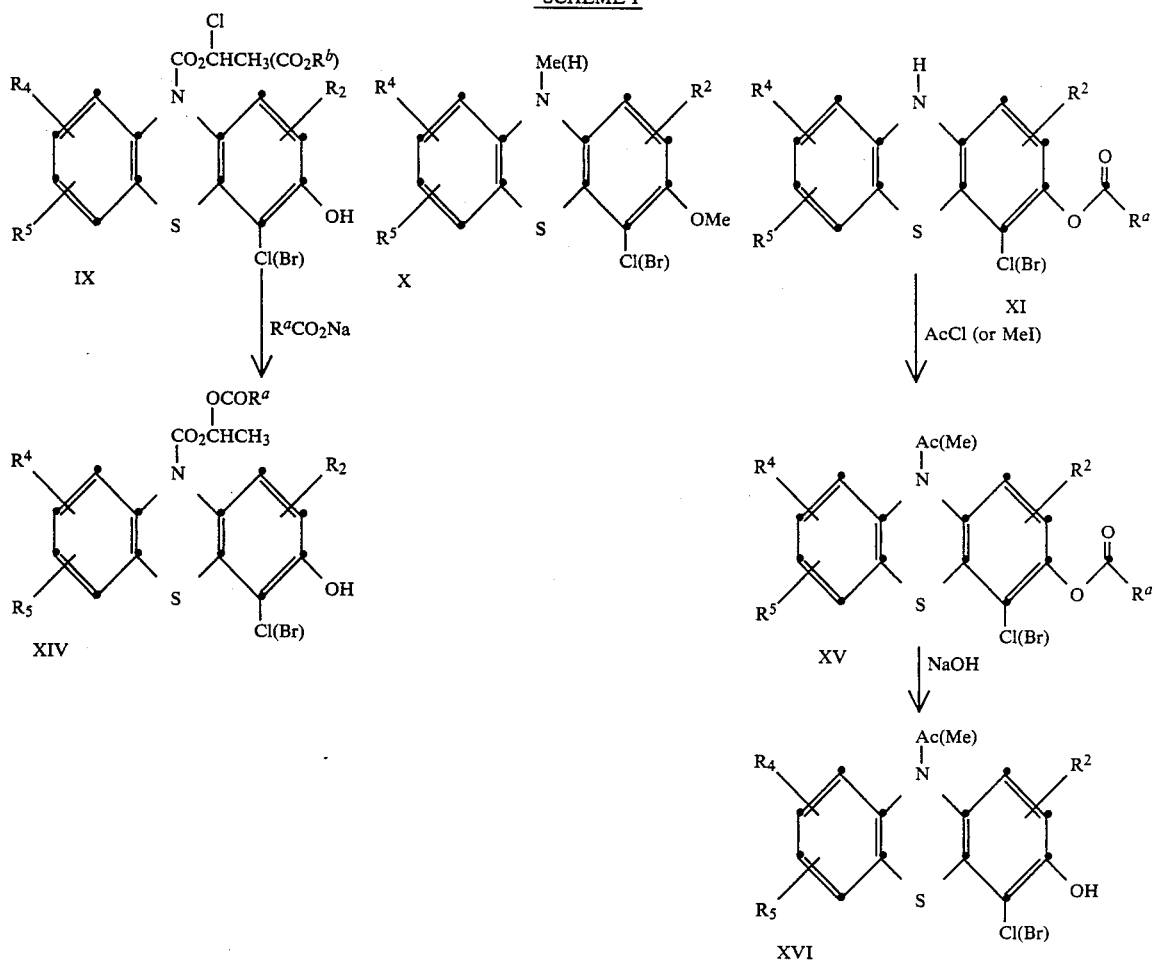

where:
$R^a$ is $C_1$ to $C_4$ alkyl or phenyl,
$R^b$ is $C_1$ to $C_4$ alkyl,
n is 1 or 2.

Reaction of a benzoquinone IV, optimally two equivalents, with 2-aminobenzenethiol V, in a solvent such as acetic acid, acetic acid-water, or a lower alkanol at from −20° to +60° C. for 0.25 to 6 hours yields the phenothiazin-3-one VI. Preferably, the solvent is methanol or ethanol, at 0° to 25° C. for 0.5 to 2 hours. Halogenation of VI to obtain VII may conveniently be carried out using chlorine or bromine in a lower alkanoic acid such as acetic acid at temperatures of 10° to 50° C. Reduction of VII to VIII is carried out with a reducing agent such as sodium hydrosulfite in a suitable solvent system by stirring at from 10° to 50° C. (preferably at room temperature) for 1 to 12 hours (preferably 1 to 4 hours). The solvent system may be a homogeneous one such as dimethylformamide-water or a two-phase system such as ethyl acetate-water or dichloromethane-water.

To prepare a carbamate derivative such as IX, compound VIII is reacted with the appropriate chloroformate reagent in a suitable solvent such as tetrahydrofuran, dioxane or preferably acetonitrile and the mixture heated to reflux for 4 to 24 hours. Reaction of the appropriate chloroalkylcarbamate IX with a metal salt of a carboxylic acid then yields the acyloxyalkoxycarbonyl compound XIV. Preferred salts are those of silver, mercury (II) or sodium, using the corresponding free acid as a solvent, and heating the reaction mixture at 0° to 100° C. for from 10 minutes to 2 hours.

To obtain the N,O-dimethylated compounds X, compound VIII is reacted with a methyl halide or a methyl sulfonate (preferably methyl iodide) in the presence of a strong base such as sodium hydride or potassium t-butoxide in a solvent such as tetrahydrofuran or dimethylformamide at 0° to 60° C. (preferably room temperature) for from 1 to 24 hours (preferably 1 to 10 hours). The O-methylated compounds X are obtained by substituting a weaker base such as $Na_2CO_3$ or $K_2CO_3$ for sodium hydride or potassium t-butoxide, and stirring at room temperature for 0.25 hours to 5 hours.

The O-acyl compounds XI are prepared by reacting compound VIII with the desired acid anhydride in pyridine at a temperature of from −25° to +75° C. (preferably 0° to 50° C.) for from 1 hour to 24 hours (preferably 4 to 15 hours). Compound XI is transformed into compound XV by reacting it with an acyl halide (bromide or chloride) in a solvent such as dichloromethane, 1,2-dichloroethane or chloroform (preferably dichloromethane) in the presence of 4 Angstrom molecular sieves for a period of 0.5 to 24 hours (preferably 1 to 6 hours) at a temperature of 0° to 60° (preferably room temperature). Hydrolysis of XV to XVI is carried out by reaction with a base such as LiOH, NaOH or KOH, in mixed solvent such as methanol-water or ethanol-water, at from 0° to 60° C. (preferably room temperature) for from 5 minutes to 180 minutes (preferably 10 minutes to 90 minutes). Alternatively, the N-acetyl compound XVI can be prepared from VIII by reacting the latter with an acyl halide, such as acetyl chloride, in a solvent such as dimethyl formamide at from 0° to 50° C. (preferably room temperature) for from 0.5 to 4 hours depending on the rate of reaction of the particular components.

The N,O-diacyl compound XV can also be prepared directly from VIII by treating a mixture of VIII and the appropriate acyl halide in a solvent such as dimethylformamide at from 50° to 150° C. (preferably 75° to 100° C.) for from 2 to 24 hours, preferably from 5 hours to 24 hours to ensure completion of the reaction.

The sulfoxide derivatives XII (n=1) are prepared by treating XI with a peracid such as peracetic acid or meta-chloroperbenzoic acid (MCPBA), in a solvent such as methylene chloride or methylene chloride-methanol for 0.5 to 4 hours at 0° to 30° C. The sulfones XII (n=2) are obtained by reacting XI with a peracid in methylene chloride-methanol, or preferably 1,2-dichloroethane-ethanol, at the reflux temperature of the mixture for 12 to 24 hours, depending upon the rate of reaction. Hydrolysis of XII to XIII is carried out in a manner similar to that described for the conversion of XV to XVI.

The following examples are provided to aid in the interpretation of the claims appearing below. They are not intended as a limitation upon the scope of said claims. Temperatures are in degrees Celsius.

Some of the 3H-phenothiazin-3-one derivatives used as starting materials are described in our co-pending applications U.S. Ser. No. 591,134, filed March 19, 1984 and European Patent Application 84300239.5, published on Aug. 8, 1984 under publication number 0115394. The disclosure of these applications is hereby incorporated herein by reference.

EXAMPLE 1

Synthesis of 3H-phenothiazin-3-one

To a stirring suspension of 1.72 kg (16 mol) of p-benzoquinone in 13 liters MeOH at room temperature was added slowly a solution of 1.0 kg (8 mol) of 2-aminothiophenol in 600 ml MeOH over a period of 1 hour. The resulting red mixture was stirred at room temperature for another 2 hours and then the product 3H-phenothiazin-3-one was filtered off. This 3H-phenothiazin-3-one was washed thoroughly with methanol and dried to give 1.07 kg of 3H-phenothiazin-3-one (61.49% yield), m.p. 157°–159° C.

EXAMPLE 2

Synthesis of 4-chloro-3H-phenothiazin-3-one

To a stirring solution of 500 g (2.34 mol) of 3H-phenothiazin-3-one in 12.5 liters of glacial acetic acid was added 1.25 kg of potassium dichromate. The mixture was stirred at room temperature for ½ hour. To this resulting mixture was then added 2.34 mol of a 1M solution of chlorine in glacial acetic acid dropwise over a period of 4 hours. The progress of the reaction was monitored by tlc to ensure no excess chlorine was added. After addition of chlorine was completed the mixture was stirred at room temperature for another ½ hour and was then poured into 120 liters of $H_2O$ with vigorous stirring. The 4-chloro-3H-phenothiazin-3-one which precipitated was allowed to settle overnight. The majority of the aqueous solution was siphoned off and discarded and the rest was filtered. The filtered precipitate was washed thoroughly with water and then rinsed with methanol and was allowed to dry to give 504 g crude 4-chloro-3H-phenothiazin-3-one which was recrystallized from toluene. m.p.: 221° C.

EXAMPLE 3

Synthesis of 4-Chloro-3-hydroxy-10H-phenothiazine

A solution of $Na_2S_2O_4$ (70 g) in water (500 ml) was added to a solution of 4-chloro-3H-phenothiazin-3-one (50 g) in DMF (1200 ml). The reaction mixture was stirred at room temperature for 3 hours and then poured in 5 liters of water. The resulting precipitate was then filtered to give the 4-chloro-3-hydroxy-10H-phenothiazine (95 %). m.p.: 110° C.

EXAMPLE 4

Synthesis of 3-acetoxy-4-chloro-10H-phenothiazine

To a solution of 1.8 g of 4-chloro-3-hydroxy-10H-phenothiazine (see Example 3) in 20 ml of acetic anhydride was added 1.2 ml of pyridine. The reaction mixture was then stirred at ambient temperature for 12 hours and then poured in water (75 ml). The resulting precipitate was filtered, washed with water and dried under vacuum to give 1.65 g of 3-acetoxy-4-chloro-10H-phenothiazine (m.p.: 173° C.).

EXAMPLE 5

Synthesis of 4-chloro-3-methoxy-10-methyl-10H-phenothiazine

To 25 ml of DMF was added methyl iodide (2.9 ml), 4-chloro-3-hydroxy-10H-phenothiazine (see Example 3) (2.3 g) and sodium hydride (0.672 g). The resulting reaction mixture was stirred at ambient temperature for 12 hours. At 0° C., MeOH was added to destroy the remaining hydride, then $H_2O$. The resulting solution was extracted with ethyl acetate and the organic phase, dried and evaporated. The resulting residue was then purified by chromatography on silica gel to give 1.5 g of 4-chloro-3-methoxy-10-methyl-10H-phenothiazine (m.p.: 136° C.).

EXAMPLE 6

Synthesis 4-chloro-3-methoxy-10-acetyl-10H-phenothiazine

To a solution of 4-chloro-3-acetoxy-10H-phenothiazine (see Example 4) in DMF (10 mls) was added methyl iodide (0.34 ml) and sodium hydride (114 mg). The reaction mixture was stirred at ambient temperature for 12 hours. Methanol and water were then added and the resulting mixture extracted with EtOAc. The organic phases were then collected, dried and evaporated. The resulting residue was purified by chromatography on silica gel (HPLC) to give 0.56 g of 4-chloro-3-methoxy-10-acetyl-10H-phenothiazine (m.p. 136° C.).

EXAMPLE 7

Synthesis of 3-benzoyloxy-4-chloro-10H-phenothiazine

To a solution of (0.5 g)4-chloro-3-hydroxy-10H-phenothiazine (see Example 3) in pyridine (4 ml) was added 1.2 g of benzoic anhydride. The reaction mixture was stirred at ambient temperature for 7 hours and then poured in $H_2O$. The resulting precipitate was then filtered and purified by trituration in $CHCl_3$. The resulting solid material was then filtered and dried under vacuum to give 0.6 g of 3-benzoyloxy-4-chloro-10H-phenothiazine (m.p. 203° C.).

EXAMPLE 8

Synthesis of 4-chloro-3-isobutyryloxy-10H-phenothiazine

To a solution of iso-butyric acid (1.6 ml) in THF (10 ml) at 0° C. was added Et₃N (2.7 ml) and methylchloroformate (1.5 ml). To this resulting suspension was added slowly at 0° C. a solution of 4-chloro-3-hydroxy-10H-phenothiazine in THF (10 ml). The reaction mixture was stirred at 5° C. for 12 hours, after which H₂O was added and the resulting aqueous phase extracted with ethyl acetate. The organic layer was then dried and evaporated. The resulting residue was purified by chromatography on silica gel to give 2.25 g of 4-chloro-3-isobutyryloxy-10H-phenothiazine (m.p. 155° C.).

EXAMPLE 9

Synthesis of 4-chloro-3-isobutyryloxy-10-methyl-10H-phenothiazine

To a solution of 4-chloro-3-isobutyrylox-10H-phenothiazine (see Example 8) (202 mg) in DMF (5 ml) was added methyl iodide (0.2 ml) and sodium hydride (18 mg) at 0° C. The reaction mixture was stirred at ambient temperature for 12 hours. To the reaction mixture was added water and the resulting aqueous layer extracted with EtOAc. The organic layers were collected, dried and evaporated to give a residue which was purified by chromatography on silica gel (plates) to give 100 mg of 4-chloro-3-isobutyryloxy-10-methyl-10H-phenothiazine (m.p. 147° C.).

EXAMPLE 10

Synthesis of 3-acetoxy-10-acetyl-4-chloro-10H-phenothiazine

To 1.1 g of 3-acetoxy-4-chloro-10H-phenothiazine (see Example 4) was added acetyl chloride (7 ml), DMF (5 ml) and potassium tert-butoxide (0.42 g). The reaction mixture was stirred at ambient temperature for 1 hour and then, poured in water. The resulting precipitate was filtered and purified by chromatography on silica gel to give (1.08 g) 3-acetoxy-10-acetyl-4-chloro-10H-phenothiazine (m.p. 155° C.).

EXAMPLE 11

Synthesis of 10-acetyl-4-chloro-3-hydroxy-10H-phenothiazine

To a solution of 4-chloro-3-hydroxyphenothiazine (2.2 g) in DMF (10 ml) was added 10 ml of acetyl chloride. The reaction mixture was stirred at ambient temperature for 1 hour. Ethyl acetate was then added, followed by ice and H₂O. The organic layer was separated, dried and evaporated. The resulting residue was purified by chromatography on silica gel to give 1.4 g of 10-acetyl-4-chloro-3-hydroxy-10H-phenothiazine (m.p. 214° C.).

EXAMPLE 12

Synthesis of 4-chloro-5,5-dioxo-3-methoxy-10-methyl-10H-phenothiazine

To 4-chloro-3-methoxy-10-methyl-10H-phenothiazine (see Example 5) (0.33 g) in acetic acid (10 ml) was added hydrogen peroxide (3 ml). The reaction mixture was stirred at 80° C. for 2 hours. After cooling to ambient temperature, the resulting precipitate was filtered and washed with acetic acid to give the 4-chloro-5,5-dioxo-3-methoxy-10-methyl-10H-phenothiazine (0.2 g) (m.p. 244° C.).

EXAMPLE 13

Synthesis of 4-chloro-3-methoxy-10-methyl-5-oxo-10H-phenothiazine

To 4-chloro-3-methoxy-10-methyl-10H-phenothiazine (0.5 g)(see Example 5) was added acetic acid (12 ml) and hydrogen peroxide (2 ml). The reaction mixture was heated at 50° C. for 15 minutes and then, evaporated to dryness. The corresponding sulfoxide (0.5 g) (4-chloro-3-methoxy-10-methyl-5-oxo-10H-phenothiazine) was obtained by crystallization (m.p. decomposed at 141° C.).

EXAMPLE 14

Synthesis of 2-chloro-3,7-diacetyl-10-methyl-10H-phenothiazine

To 2-chloro-10-methyl-10H-phenothiazine (5 g) in carbon disulfide (100 ml) was added acetyl chloride (2.2 ml) and (portionwise) aluminum chloride (10 g). The reaction mixture was then stirred under reflux for 12 hours. The carbon disulfide was then decanted and the residue treated with ice and concentrated HCl. The resulting precipitate was filtered, washed with water and purified by chromatography on silica gel to yield the title compound, m.p. 185° C.

EXAMPLE 15

Synthesis of 4-chloro-3-methoxy-10-methyl-10H-phenoxazine

This compound was prepared as described in Example 5 following the sequence exemplified in Examples 2 and 3, but starting with 3H-phenoxazine-3-one, instead of 3H-phenothiazine-3-one. The title compound, 4-chloro-3-methoxy-10-methyl-10H-phenoxazine was then obtained (m.p. 107° C.).

EXAMPLE 16

Synthesis of 3,4-dihydroxy-10H-phenothiazine-5,5-dioxide

To a suspension of 4-hydroxy-3H-phenothiazine-3-one-5,5-dioxide (0.8 g) in a mixture of water (20 ml) and ethyl acetate (20 ml) there was added sodium dithionite (2 g) and the resulting mixture was stirred at room temperature for 20 minutes. The insoluble solid was then filtered, washed with water and dried to afford the title compound, m.p. (dec.) 261° C.

Calc'd: C: 54.74; H: 3.45; N: 5.32; S: 12.18: Found: C: 54.85; H: 3.54; N: 5.26; S: 12.11.

EXAMPLE 17

Synthesis of 2,4-di-t-butyl-1-hydroxy-10H-phenothiazine

To a solution of 3,5-di-t-butyl-1,2-benzoquinone (2.2 q) in methanol (15 ml) cooled in an ice bath was added 2-aminothiophenol (1.38 g) and the mixture was stirred for 2 hours. A solid precipitate was filtered off and crystallized from heptane to yield the title compound m.p. 202°–212° (dec.). From the methanol filtrate there was obtained, after chromatography and crystallization, an additional crop of the title compound.

EXAMPLE 18

Synthesis of 4-bromo-2,7-dimethoxy-3-hydroxy-10H-phenothiazine

Step 1: Preparation of 2-methoxy-p-benzoquinone

Vanillin (2.432 kg) was added to a solution of sodium hydroxide (640 g) in water (8 l) and cooled to 10° C. with an ice-bath. Then a solution of hydrogen peroxide (30%) (2.4 l) was added at a rate to keep the temperature of the reacting mixture below 30° C. The addition completed (about 2 hours), the reaction mixture was added over a period of 3 hours to a suspension of sodium periodate (880 g) in water (4 l) and acetic acid (640 ml) cooled with an ice-bath to 10° C. (the temperature of the reacting mixture was kept below 35° C.). The resulting precipitate was filtered, washed with cold water followed by ethanol/hexane (1:1) mixture and air-dried to afford the title compound (1.9 kg), m.p. 144°–147° C.

Step 2: Preparation of 2-amino-5-methoxythiophenol

To a stirred solution of 8N potassium hydroxide (1.3 l) was added 2-amino-6-methoxybenzothiazole (750 g) and the mixture was refluxed overnight. The resulting solution was neutralized by the addition of conc. HCl to pH 8.0, then acetic acid to pH 6.0. The precipitate which formed was filtered and washed with water to afford the title compound which was used immediately in Step 3.

Step 3: Preparation of 2,7-dimethoxy-3H-phenothiazin-3-one

To a suspension of 2-methoxy-p-benzoquinone (1.15 kg) (Step 1) in methanol (8 l) was added portionwise a suspension of 2-amino-5-methoxythiophenol (from Step 2) in methanol (6 l). The reacting mixture was stirred for 15 minutes, filtered and washed with methanol (8 l). The product isolated was swished with DMF (16 l) for 2 hours, filtered and air-dried. The crude material was dissolved in hot DMF (16 l) (130°–140° C.), filtered on Celite and the filtrate cooled to room temperature. The resulting crystals were filtered, washed with methanol (8 l) and air-dried to afford the title compound (70.3 g), m.p. 237°–238° C.

Step 4: Preparation of 4-bromo-2,7-dimethoxy-3H-phenothiazin-3-one

A solution of bromine (280 g) in acetic acid (2.8 l) was added over a period of 30 minutes to a suspension of 2,7-dimethoxy-3H-phenothiazin-3-one (250 g) (Step 3) in acetic acid (7.5 l) and the mixture was stirred for 2 hours. Methanol (12 l) was added over a period of 30 minutes to the reacting mixture and the black suspension was stirred until it became an orange suspension. Then, the precipitate was filtered, washed with methanol and air-dried to afford the desired compound (312 g), m.p. 260°–261° C.

Calc'd: C, 47.74; H, 2.86; N, 3.98; S, 9.10; Br, 22.69.
Observed: C, 47.74; H, 2.81; N, 3.90; S, 9.02; Br, 22.37.

Step 5: Preparation of 4-bromo-2,7-dimethoxy-3-hydroxy-10H-phenothiazine

The compound from Step 4 (300 mg) was suspended in ethyl acetate (100 ml) and a solution of $Na_2S_2O_4$ (2 g) in water (40 ml) was then added and the mixture was shaken until the orange-red coloration disappeared. The aqueous layer was decanted, the organic layer was washed with water, dried and evaporated to dryness. The resulting residue was treated with ether and filtered to afford the title compound (240 mg), m.p. 185° C.

Calc'd: C, 47.47; H, 3.42; N, 3.95; S, 9.05; Br, 22.56;
Observed: C, 47.21; H, 3.39; N, 3.74; S, 8.76; Br, 22.44.

EXAMPLE 19

Synthesis of 3-Acetoxy-4-bromo-2,7-dimethoxy-10H-phenothiazine

Using the procedure of Example 4, but substituting 4-bromo-2,7-dimethoxy-3-hydroxy-10H-phenothiazine for 4-chloro-3-hydroxy-10H-phenothiazine, the title compound was obtained. m.p. 201°–203° C.

EXAMPLE 20

Synthesis of 3-Acetoxy-2,7-dimethoxy-10H-phenothiazine

Following the procedure of Example 4, but substituting 2,7-dimethoxy-3-hydroxy-10H-phenothiazine for 4-chloro-3-hydroxy-10H-phenothiazine, the title compound was obtained. m.p. 172°–174° C.

EXAMPLE 21

Synthesis of 3-Benzoyloxy-4-bromo-2,7-dimethoxy-10H-phenothiazine

Following the procedure described in Example 7, but substituting 4-bromo-2,7-dimethoxy-3-hydroxy10H-phenothiazine for 4-chloro-3-hydroxy-10H-phenothiazine, and heating for 3 hours at 100° C., the title compound was obtained. m.p. 202°–203° C.

Calc'd: C, 55.03; H, 3.52; N, 3.05; S, 7.00; Br, 17.44:
Found: C, 54.99; H, 3.45; N, 3.06; S, 6.73; Br, 17.57.

EXAMPLE 22

Synthesis of 4-Bromo-10-methyl-2,3,7-trimethoxy-10H-phenothiazine

Following the procedure described in Example 5, but substituting 4-bromo-2,7-dimethoxy-3-hydroxy-10H-phenothiazine for 4-chloro-3-hydroxy-10H-phenothiazine and potassium t-butoxide for sodium hydride, the title compound was obtained. m.p. 143°–145° C.

Calc'd: C, 50.27; H, 4.22; N, 3.66; S, 8.39; Br, 20.91:
Found: C, 50.50; H, 4.11; N, 3.67; S, 8.35; Br, 20.83.

EXAMPLE 23

Synthesis of 4-Bromo-2,3,7-trimethoxy-10H-phenothiazine

To a solution of 4-bromo-2,7-dimethoxy-3-hydroxy-10H-phenothiazine (3.54 g) and methyliodide (2.5 ml) in DMF (20 ml) there was added pulverized potassium carbonate (1.3 g). The reaction mixture was stirred at room temperature. After 15 minutes, another addition of potassium carbonate (1 gram) was made, followed by two other such additions at 15-minute intervals. The final mixture was stirred for a further 15 minutes, then it was diluted with water (100 ml) and ethyl acetate (100 ml). The organic layer was washed twice with water, dried and evaporated down to a solid residue. Crystallization from acetone followed by column chromatography on silica gel eluting with 1:19 ethyl acetate-dichloromethane afforded the pure title compound (1.27 g). m.p. 223°–225° C.

Calc'd: C, 48.92; H, 3.83; N, 3.80; S, 8.71; Br, 21.70:
Found: C, 48.83; H, 3.76; N, 3.68; S, 8.57; Br, 21.80.

EXAMPLE 24

Synthesis of
10-Acetyl-4-Bromo-2,3,7-trimethoxy-10H-phenothiazine

Following the procedure described in Example 6, but substituting 3-acetoxy-4-bromo-2,7-dimethoxy-10H-phenothiazine for 3-acetoxy-4-chloro-10H-phenothiazine and potassium t-butoxide for sodium hydride, the title compound was obtained. m.p. 147°–149° C.

EXAMPLE 25

Synthesis of
3-Acetoxy-4-Bromo-2,7-dimethoxy-10-methyl-10H-phenothiazine and
4-bromo-10-methyl-2,3,7-trimethoxy-10H-phenothiazine To a solution of 3-acetoxy-4-bromo-2,7-dimethoxy-10H-phenothiazine (8.0 g) in N,N-dimethylformamide (80 ml) there was added at room temperature methyl iodide (16 ml) and then potassium t-butoxide (3 g). The mixture was stirred at room temperature. Over a period of 24 hours, seven further additions of methyl iodide (10 ml) and potassium t-butoxide (2 g) were made. The final reaction mixture was diluted with ethyl acetate and the solids filtered. The filtrate was washed three times with brine, dried and evaporated. Flash chromatography of the residue on a column of silica gel, eluting with a 1:9 mixture of ethyl acetate and hexane afforded 3-acetoxy-4-bromo-2,7-dimethoxy-10-methyl-10H-phenothiazine (830 mg, m.p. 189°–190° C.) and 4-bromo-10-methyl-2,3,7-trimethoxy-10H-phenothiazine (2.86 g, m.p. 135°–137° C.).

EXAMPLE 26

Synthesis of
4-bromo-2,7-dimethoxy-3-hydroxy-10-methyl-10H-phenothiazine

To a suspension of 3-acetoxy-4-bromo-2,7-dimethoxy-10-methyl-10H-phenothiazine (0.5 g) in methanol (300 ml) there was added 2N aqueous sodium hydroxide (300 ml) and the mixture was stirred at room temperature overnight. The heterogenous mixture was then acidified with 1N aqueous HCl solution, and after stirring for 15 minutes the product filtered. This crude product was purified by flash chromatography on a column of silica gel, eluting with a 1:1 mixture of ethyl acetate and hexane, and the pure title product (211 mg) was obtained. m.p. 154°–155° C.

EXAMPLE 27

Synthesis of
3-acetoxy-10-acetyl-4-bromo-2,7-dimethoxy-10H-phenothiazine

Method A: To a solution of 3-acetoxy-4-bromo-2,7-dimethoxy-10H-phenothiazine (8.0 g) in 1,2-dichloroethane (300 ml) there was added acetyl bromide (1.79 ml) and powdered 4 Angstrom molecular sieves (20 g). The resulting mixture was stirred at room temperature for 2 hours, then filtered. The filtrate was evaporated and the residue co-evaporated with acetone twice. It was then crystallized from dichloromethane-hexane to afford the pure title compound (7.0 g). m.p.: 185°–187° C.

Method B: To a solution of 3-hydroxy-4-bromo-2,7-dimethoxy-10H-phenothiazine (180 g) in dimethylformamide (1.2 L) was added acetyl chloride (230 mL) and the resulting solution was heated at 85° C. for 18 hours. The excess of acetyl chloride was removed under vacuum and the remaining solution was poured slowly onto an ice-water mixture (1:1) (4L) with good mechanical stirring. The resulting precipitate was filtered, dissolved in dichloromethane, dried over sodium sulfate and concentrated under vacuum. The oily residue was dissolved in ether and left to crystallize overnight. The crystals were filtered to afford the title compound (186 g). A sample (10 g) was recrystallized from ethyl acetate to afford the pure product (7 g).

EXAMPLE 28

Synthesis of
10-acetyl-4-bromo-2,7-dimethoxy-3-hydroxy-10H-phenothiazine

A mixture of 10-acetyl-3-acetoxy-4-bromo-2,7-dimethoxy-10H-phenothiazine (2.0 g) in methanol (40 ml) and 1N aqueous sodium hydroxide solution (40 ml) was stirred at room temperature for 5 hours. The mixture was then made slightly acidic with 1N aqueous HCl and after 15 minutes the crude product was filtered. Crystallization from ethyl acetate afforded the pure title compound (600 mg), m.p.: dec 235° C.

EXAMPLE 29

Synthesis of
10-(1-acetoxyethoxycarbonyl)-4-bromo-2,7-dimethoxy-3-hydroxy-10H-phenothiazine Step 1: Preparation of α-chloroethylchloroformate To a mixture of ethyl chloroformate (108.5 g) and sulfuryl chloride (138 g), benzoyl peroxide (1 g) was added and the mixture was refluxed for 20 hours. The reaction mixture was distilled and the liquid boiling above 110° was collected. This was then fractionated using a 30 cm column packed with glass helices to give 32 g of pure α-chloroethyl chloroformate (b.p. 118°–119°).

Step 2: Preparation of 4-bromo-10-(1-chloroethoxy carbonyl)-2,7-dimethoxy-3-hydroxy-10H-phenothiazine A mixture of 4-bromo-2,7-dimethoxy-3-hydroxy-10H-phenothiazine (5 g) α-chloroethyl chloroformate (7 g) in THF (50 ml) was refluxed for 18 hours. The mixture was then concentrated to a small volume and flash-chromatographed on a column of silica gel to afford the desired product as a solid which was used directly in the next step.

Step 3:
10-(1-acetoxyethoxycarbonyl)-4-bromo-2,7-dimethoxy-3-hydroxy-10H-phenothiazine A mixture of 4-bromo-10-(1-chloroethoxycarbonyl)-2,7-dimethoxy-3-hydroxy-10H-phenothiazine (1g) and mercuric acetate (1.46g) in glacial acetic acid (30 ml) was stirred and heated at 85° for 10 minutes. After cooling the mixture was diluted with ethyl acetate, washed with water, aqueous NaHCO3 solution, and brine, dried and evaporated. Flash chromatography on a column of silica gel, eluting with a 1:3 mixture of ethyl acetate and hexane, afforded the pure title product (599 mg) m.p.: 162°–164° C.

EXAMPLE 30

Synthesis of 3-acetoxy-10-(1-acetoxyethoxycarbonyl)-4-bromo-2,7-dimethoxy-10H-phenothiazine By following the procedures described in steps 2 and 3 of example 29, substituting 3-acetoxy-4-bromo-2,7-dimethoxy-10H-phenothiazine for the 3-hydroxy analog, the title compound was obtained. m.p.: 134°–135° C.

EXAMPLE 31

Synthesis of 3-acetoxy-4-bromo-2-methoxy-7-methyl-10H-phenothiazine

Following the procedure described in Example 3, but substituting 4-bromo-2-methoxy-7-methyl-3H-phenothiazin-3-one for 4-chloro-3H-phenothiazin-3-one, there was obtained the intermediate 4-bromo-3-hydroxy-2-methoxy-7-methyl-10H-phenothiazine, which when used as starting material in the procedure described in Example 4 afforded the title compound. m.p.: 193°–194° C.

EXAMPLE 32

Synthesis of 3-acetoxy-4-bromo-7-fluoro-2-methoxy-10H-phenothiazine

Following the procedure described in example 31, but substituting 4-bromo-7-fluoro-2-methoxy-3H-phenothiazine-3-one for the 7-methyl analog, there was obtained the intermediate 4-bromo-7-fluoro-3-hydroxy-2-methoxy-10H-phenothiazine, which was used as starting material in the procedure described in Example 4 to afford the title compound. m.p.: 224°–226° C.

EXAMPLE 33

Synthesis of 3-acetoxy-4-bromo-2,7-dimethoxy-10H-phenothiazine-5-oxide

To a solution of 3-acetoxy-4-bromo-2,7-dimethoxy-10H-phenothiazine (10.0 g) in dichloromethane (125 ml) and methanol (125 ml) there was added at room temperature 85% m-chloro peroxybenzoic acid (4.36 g). The mixture was stirred for one hour and the solid was filtered and washed with ether. This crude product was stirred at room temperature in dichloromethane (50 ml) overnight and filtered again to afford pure title product (7.7g). m.p.: 243°–247° C. (dec).

EXAMPLE 34

Synthesis of 3-acetoxy-4-bromo-2,7-dimethoxy-10H-phenothiazine-5,5-dioxide

To a solution of 3-acetoxy-4-bromo-2,7-dimethoxy-10H-phenothiazine (20.0 g) in dichloromethane (250 ml) and methanol (250 ml) there was added 85% m-chloroperoxy benzoic acid (26.0 g) and the resulting mixture stirred at reflux temperature for 18 hours. After cooling, the insoluble solid was collected by filtration. It was suspended in 1,2-dichloroethane (250 ml) and ethanol (250 ml) and there was again added 85% m-chloroperoxybenzoic acid (1.35g). The mixture was refluxed for 18 hours, cooled and filtered to afford the title product (13.0g).

m.p.: 258°–260° C.

Calc'd. C: 44.87; H: 3.29; N: 3.27; S: 7.49: Found C: 44.82; H: 3.21; N: 3.18; S: 7.67.

EXAMPLE 35

Synthesis of 4-bromo-2,7-dimethoxy-3-hydroxy-10H-phenothiazine-5,5-dioxide

To a suspension of 3-acetoxy-4-bromo-2,7-dimethoxy-10H-phenothiazine-5,5-dioxide (10.0 g) in methanol (105 ml) there was added 2N aqueous sodium hydroxide solution (74 ml) and the resulting mixture was stirred at room temperature for 20 minutes. There was then added 10% aqueous acetic acid solution (250 ml) and a thick precipitate was formed. The mixture was diluted with water (105 ml) and filtered, the solid washed with water and ether, and dried in a desiccator, affording the title compound (9.6 g). Further purification of a small sample was achieved through chromatography on a short column of silica gel, eluting with acetone. m.p.: 252°–260° (dec).

EXAMPLE 36

Synthesis of 3-acetoxy-2,7-dimethoxy-10H-phenothiazine-5-oxide

The procedure of Example 33 was employed, substituting 3-acetoxy-2,7-dimethoxy-10H-phenothiazine for the 4-bromo analog, to afford the title compound.

m.p.: 238° C. (dec).

EXAMPLE 37

Synthesis of 3-acetoxy-2,7-dimethoxy-10H-phenothiazine-5,5-dioxide

Following the procedure described in Example 34, but substituting 3-acetoxy-2,7-dimethoxy-10H-phenothiazine for the 4-bromo analog, there was obtained the title compound. m.p.: 265°–268° C.

EXAMPLE 38

Synthesis of 2,7-dimethoxy-3-hydroxy-10H-phenothiazine-5,5-dioxide

Using the procedure described in example 35, but substituting 3-acetoxy-2,7-dimethoxy-10H-phenothiazine-5,5-dioxide for the 4-bromo analog, there was obtained the title compound. m.p.: 276°–278° C. (dec).

Following the procedures described above, the following compounds were prepared:

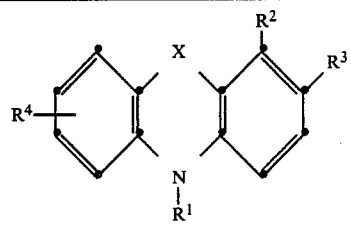

| Example No. | X | $R^1$ | $R^2$ | $R^3$ | $R^4$ | m.p. (°C.) |
|---|---|---|---|---|---|---|
| 39 | S | Me | Cl | OAc | H | 132 |
| 40 | S | Me | H | OMe | 7-F | 104 |

-continued

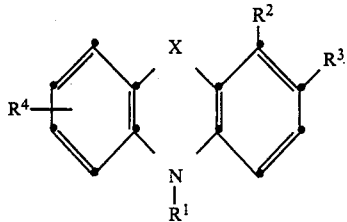

| Example No. | X | R¹ | R² | R³ | R⁴ | m.p. (°C.) |
|---|---|---|---|---|---|---|
| 41 | S | Ac | H | OMe | 7-F | 92 |
| 42 | S | Ac | H | OH | 7-F | 195 |
| 43 | S | Ac | H | OAc | 7-F | 144–145 |
| 44 | S | Me | H | OMe | 7-Me | 102 |
| 45 | S | H | H | OAc | 7-F | 175–176 |
| 46 | S | Me | H | OMe | 9-Cl | 59 |
| 47 | S | Me | H | OAc | 9-Cl | 87–88 |
| 48 | S | Me | H | OAc | 7-Me | 108–110 |
| 49 | S | H | H | OAc | 9-Cl | 117 |
| 50 | S | H | CF₃ | OAc | H | 133 |
| 51 | S | H | Cl | OTs | H | 178 |
| 52 | S | Ac | Cl | OMe | 7-F | 206 |
| 53 | S | Ac | Cl | OH | 7-F | 209 |
| 54 | S | Me | Cl | OMe | 7-F | 122 |
| 55 | SO | H | H | OAc | H | 220 |
| 56 | SO₂ | H | H | OAc | H | 254–256 |
| 57 | SO₂ | H | Cl | OAc | H | 274–277 |
| 58 | SO₂ | H | Cl | OH | H | 286 |
| 59 | SO₂ | H | H | OH | 7-F | >220 |
| 60 | SO₂ | H | H | OAc | 7-F | 222 |
| 61 | SO₂ | H | Cl | OTs | H | >240 |
| 62 | SO₂ | H | OH | OH | H | 261 |
| 63 | SO₂ | H | OMe | OH | H | 279 |

EXAMPLE 64

Synthesis of 4-chloro-2-ethoxy-3-hydroxy-10H-phenothiazine

By following the procedure described in Step 5 of Example 18, but substituting 4-chloro-2-ethoxy-3H-phenothiazin-3-one for 4-bromo-2,7-dimethoxy-3H-phenothiazin-3-one, the title compound was obtained. m.p. 186°–189° C.

EXAMPLE 65

Synthesis of 1,2-dimethoxy-3-hydroxy-4-methyl-10H-phenothiazine, 5,5-dioxide

Starting with 1,2-dimethoxy-4-methyl-3H-phenothiazin-3-one, and using the procedures described in Step 5 of Example 18, Example 19, Example 34 and Example 26, the title compound was obtained. m.p. 218°–220° C.

EXAMPLE 66

Synthesis of 4-Bromo-2,7-dimethoxy-3-hydroxy-10-(1-pivaloyloxyethoxycarbonyl)-10H-phenothiazine Following the procedure of Example 29, Step 3, but substituting sodium pivaloate in place of mercuric acetate and pivalic acid in place of acetic acid, and heating at 85° for 4 hours, the title compound was obtained, m.p. 85°.

What is claimed is:

1. A method of inhibiting mammalian leukotriene biosynthesis or action which comprises administering a composition containing a pharmaceutical carrier and an effective amount of a compound of Formula I:

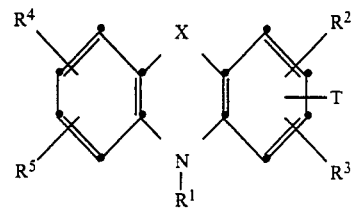

wherein:
X is Se, S, SO, SO₂ or O;
R¹ is H; $C_1$ to $C_6$ alkyl; $C$ to $C_6$ acyl; lower acyloxy-lower alkyl; lower alkoxy-lower alkyl

C-phenyl; C-substituted phenyl wherein substituted phenyl is as defined in the definition of $R_{16}$; carbamoyl;

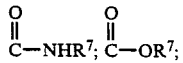
C—NHR⁷; C—OR⁷;

$SO_2$-$C_6H_4$-p-$CH_3$; $SO_2CH_3$; an acyl group such that $R^1$-OH is an essential amino acid; benzyl; phenethyl; $(CH_2)_nOR^a$ wherein $R^a$ is $C_1$ to $C_6$ alkyl or phenyl and n is 1 to 5; $(CH_2)_nCOOR^6$ wherein n is 0 to 2; or lower acyloxy-lower alkoxy carbonyl;

$R^2$, $R^3$, $R^4$ and $R^5$ are independently selected hydrogen,
 (1) hydrogen;
 (2) alkyl having 1 to 6 carbon atoms;
 (3) alkenyl having 2 to 6 carbon atoms; and
 (4) —$(CH_2)_nM$
wherein n is 0 to 6 and M is
 (a) —$OR^{16}$;
 (b) halogen;
 (c) —$CF_3$;
 (d) —$SR^{16}$;
 (e) phenyl or substituted phenyl wherein substituted phenyl is as defined in the definition of $R^{16}$;
 (f) $COOR^6$;
 (g)

C—R¹⁴;

(h) tetrazole;
 (i)

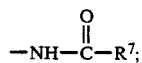
—NH—C—R⁷;

(j) —$NR^8R^9$;
 (k) —$NHSO_2R^{10}$ wherein $R^{10}$ is OH, $C_1$ to $C_6$ alkyl, $C_1$ or $C_6$ alkoxy, or phenyl;
 (l)

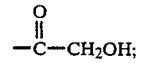
—C—CH₂OH;

(m) —$SOR^{11}$ wherein $R^{11}$ is $C_1$ to $C_6$ alkyl; phenyl; substituted phenyl wherein substituted phenyl is as defined in the definition of $R^{16}$;

$(CH_2)_mCOOR^6$ wherein m is 1 to 6, CN; formyl; or perfluoro-$C_1$ to $C_4$ alkyl; —$CONR^8R^9$;
(n) —$CONR^8R^9$;
(o) —$SO_2NR^8R^9$;
(p) —$SO_2R^{13}$ wherein $R^{13}$ is OH; $C_1$ to $C_6$ alkyl; H; phenyl; substituted phenyl wherein substituted phenyl is as defined in the definition of $R^{16}$; $(CH_2)_mCOOR^6$ wherein m is 1 to 6; CN; formyl; or perfluoro-$C_1$ to $C_4$ alkyl;
(q) —$NO_2$;
(r)

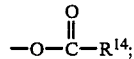

(s)

(t) —CN;
each $R^6$ is independently H, phenyl or $C_1$ to $C_6$ alkyl;
each $R^7$ is independently $C_1$ to $C_6$ alkyl, benzyl, phenyl or $C_1$ to $C_6$ acyloxy-$C_1$ to $C_6$ alkyl;
each $R^8$ and each $R^9$ is independently H, $C_1$ to $C_4$ acyl, phenyl, or substituted phenyl wherein the substituted phenyl is as defined in the definition of $R_{16}$, or an $R^8$ and an $R^9$ may be joined through the N to which they are attached to form a heterocycloalkyl group of 5 to 8 ring atoms;
each $R^{14}$ is independently H, $(CH_2)_nCOOR^6$ wherein n is 0 to 4, $C_1$ to $C_6$ alkyl; $C_1$ to $C_6$ alkoxy; $C_1$ to $C_6$ acyloxy-$C_1$ to $C_6$ alkoxy; phenyl; substituted phenyl wherein the substituted phenyl is as defined in the definition of $R^{16}$; or $C_1$ to $C_6$ aminoalkyl such that $R^{14}COOH$ is an essential amino acid;
each $R^{16}$ is indepentently H; lower alkoxy-lower alkyl; $C_1$ to $C_6$ alkyl; benzyl; lower acyloxy-lower alkyl; phenyl; substituted phenyl wherein the substituents are selected from $C_1$ to $C_3$ alkyl, halogen, CN, $CF_3$, $COOR^6$, $CH_2COOR^6$, $(CH_2)_nNR^8R^9$ wherein n is 0 to 2, $C_1$ to $C_3$ alkoxy, or OH; —$(CH_2)_mCOOR^6$, wherein m is 0 to 6; CN; formyl; perfluoroallkyl; or $CH_2$—$R^{12}$ wherein $R^{12}$ is $C_1$ to $C_5$ alkyldimethylamino or phenyl;
and T is hydrogen or —$OR^{15}$, where $R^{15}$ is hydrogen, C to $C_6$ alkyl, $C_1$ to $C_6$ alkylacyl, phenylacyl, or substituted phenyl-acyl wherein substituted phenyl is as defined in the definition of $R^{16}$ or arylsulfonyl;
and pharmaceutically acceptable salts thereof.

* * * * *